(12) United States Patent
Peterson et al.

(10) Patent No.: US 11,389,213 B2
(45) Date of Patent: Jul. 19, 2022

(54) MINIMALLY INVASIVE INSTRUMENT SET, DEVICES, AND RELATED METHODS

(71) Applicant: DePuy Synthes Products, Inc., Raynham, MA (US)

(72) Inventors: Joseph Peterson, South Dartmouth, MA (US); Ralph Solitario, Jr., Pocasset, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 16/126,574

(22) Filed: Sep. 10, 2018

(65) Prior Publication Data
US 2019/0008565 A1  Jan. 10, 2019

Related U.S. Application Data

(60) Continuation of application No. 15/202,959, filed on Jul. 6, 2016, which is a continuation of application No. 13/965,764, filed on Aug. 13, 2013, now Pat. No. 9,402,663, which is a division of application No. 12/766,393, filed on Apr. 23, 2010, now Pat. No. 8,535,318.

(51) Int. Cl.
| | |
|---|---|
| *A61B 17/70* | (2006.01) |
| *A61B 17/02* | (2006.01) |
| *A61B 17/00* | (2006.01) |
| *A61B 50/33* | (2016.01) |

(52) U.S. Cl.
CPC ........ *A61B 17/7086* (2013.01); *A61B 17/025* (2013.01); *A61B 17/0218* (2013.01); *A61B 17/7037* (2013.01); *A61B 17/7074* (2013.01); *A61B 17/7077* (2013.01); *A61B 17/7079* (2013.01); *A61B 17/7082* (2013.01); *A61B 17/7091* (2013.01); *A61B 50/33* (2016.02); *A61B 2017/0046* (2013.01); *A61B 2017/0256* (2013.01)

(58) Field of Classification Search
CPC .............. A61B 17/025; A61B 17/7077; A61B 17/7085; A61B 17/7079
See application file for complete search history.

(56) References Cited

U.S. PATENT DOCUMENTS

| | | |
|---|---|---|
| 2,250,417 A | 7/1941 | Ettinger |
| 2,373,478 A | 4/1945 | Kuhn |
| (Continued) | | |

FOREIGN PATENT DOCUMENTS

| | | | |
|---|---|---|---|
| AU | 1367295 A | 9/1995 |
| AU | 06977/05 B2 | 10/1998 |
| (Continued) | | |

OTHER PUBLICATIONS

Xia Spinal System, Stryker Howmedica Oseteonics, Stryker Spine, 1999, 8 pages.

(Continued)

*Primary Examiner* — Ellen C Hammond
(74) *Attorney, Agent, or Firm* — BakerHostetler

(57) ABSTRACT

Methods of applying a locking cap to a bone anchor assembly. The bone anchor assembly includes a bone anchor and an elongate rod. The bone anchor includes a body that defines a channel and has a tissue retractor coupled thereto that defines a partial pathway to the channel.

13 Claims, 24 Drawing Sheets

(56) References Cited

U.S. PATENT DOCUMENTS

| | | |
|---|---|---|
| 3,575,405 A | 4/1971 | Harding |
| 3,604,487 A | 9/1971 | Gilbert |
| 4,335,715 A | 6/1982 | Kirkley |
| 4,409,968 A | 10/1983 | Drummond |
| 4,411,259 A | 10/1983 | Drummond |
| 4,545,374 A | 10/1985 | Jacobson |
| 4,733,657 A | 3/1988 | Kluger |
| 4,817,587 A | 4/1989 | Janese |
| 4,827,918 A | 5/1989 | Olerud |
| 4,904,010 A | 2/1990 | Lacey et al. |
| 4,957,495 A | 9/1990 | Kluger |
| 5,015,247 A | 5/1991 | Michelson |
| 5,020,519 A | 6/1991 | Hayes et al. |
| 5,047,029 A | 9/1991 | Aebi et al. |
| D331,625 S | 12/1992 | Price et al. |
| 5,171,279 A | 12/1992 | Mathews |
| 5,207,678 A | 5/1993 | Harms et al. |
| 5,217,497 A | 6/1993 | Seyed |
| 5,219,349 A | 6/1993 | Krag et al. |
| 5,242,443 A | 9/1993 | Kambin |
| 5,254,118 A | 10/1993 | Mirkovic |
| 5,312,404 A | 5/1994 | Asher et al. |
| 5,344,422 A | 9/1994 | Frigg |
| 5,352,231 A | 10/1994 | Brumfield et al. |
| 5,360,431 A | 11/1994 | Puno et al. |
| 5,431,658 A | 7/1995 | Moskovich |
| 5,433,467 A | 7/1995 | Easterwood |
| 5,439,464 A | 8/1995 | Shapiro |
| 5,443,467 A | 8/1995 | Biedermann et al. |
| 5,474,555 A | 12/1995 | Puno et al. |
| 5,484,440 A | 1/1996 | Allard |
| 5,487,744 A | 1/1996 | Howland |
| 5,498,262 A | 3/1996 | Bryan |
| 5,501,684 A | 3/1996 | Schlapfer et al. |
| 5,507,211 A | 4/1996 | Wagner |
| 5,520,690 A | 5/1996 | Errico et al. |
| 5,529,571 A | 6/1996 | Daniel |
| 5,531,746 A | 7/1996 | Errico et al. |
| 5,547,873 A | 8/1996 | Magneson et al. |
| 5,562,661 A | 10/1996 | Yoshimi et al. |
| 5,605,458 A | 2/1997 | Bailey et al. |
| 5,607,426 A | 3/1997 | Ralph et al. |
| 5,611,800 A | 3/1997 | Davis et al. |
| 5,613,968 A | 3/1997 | Lin |
| 5,624,441 A | 4/1997 | Sherman et al. |
| 5,624,442 A | 4/1997 | Mellinger et al. |
| 5,647,873 A | 7/1997 | Errico et al. |
| 5,649,931 A | 7/1997 | Bryant et al. |
| 5,667,506 A | 9/1997 | Sutterlin |
| 5,667,513 A | 9/1997 | Torrie et al. |
| 5,669,911 A | 9/1997 | Errico et al. |
| 5,676,664 A | 10/1997 | Allard et al. |
| 5,690,630 A | 11/1997 | Errico et al. |
| 5,707,371 A | 1/1998 | Metz-Stavenhagen |
| 5,720,751 A | 2/1998 | Jackson |
| 5,725,588 A | 3/1998 | Errico et al. |
| 5,728,046 A | 3/1998 | Mayer et al. |
| 5,732,992 A | 3/1998 | Mauldin |
| 5,782,830 A | 7/1998 | Farris |
| 5,782,833 A | 7/1998 | Haider |
| 5,797,911 A | 8/1998 | Sherman et al. |
| 5,810,878 A | 9/1998 | Burel et al. |
| 5,817,094 A | 10/1998 | Errico et al. |
| 5,863,293 A | 1/1999 | Richelsoph |
| 5,876,402 A | 3/1999 | Errico et al. |
| 5,879,350 A | 3/1999 | Sherman et al. |
| 5,882,350 A | 3/1999 | Ralph et al. |
| 5,885,285 A | 3/1999 | Simonson |
| 5,885,286 A | 3/1999 | Sherman et al. |
| 5,888,204 A | 3/1999 | Ralph et al. |
| 5,910,141 A | 6/1999 | Morrison et al. |
| 5,928,139 A | 7/1999 | Koros et al. |
| 5,938,663 A | 8/1999 | Petreto |
| 5,946,988 A | 9/1999 | Metz-Stavenhagen |
| 5,951,559 A | 9/1999 | Burkhart |
| 5,964,760 A | 10/1999 | Richelsoph |
| 5,964,761 A | 10/1999 | Kambin |
| 5,991,997 A | 11/1999 | Schley et al. |
| 6,010,503 A | 1/2000 | Richelsoph et al. |
| 6,022,350 A | 2/2000 | Ganem |
| 6,030,388 A | 2/2000 | Yoshimi et al. |
| 6,053,917 A | 4/2000 | Sherman et al. |
| 6,055,456 A | 4/2000 | Gerber |
| 6,066,174 A | 5/2000 | Farris |
| 6,074,391 A | 6/2000 | Metz-Stavenhagen et al. |
| 6,077,262 A | 6/2000 | Schlaepfer et al. |
| 6,090,110 A | 7/2000 | Metz-Stavenhagen |
| 6,090,111 A | 7/2000 | Nichols |
| 6,090,113 A | 7/2000 | Le et al. |
| 6,132,432 A | 10/2000 | Richelsoph |
| 6,139,493 A | 10/2000 | Koros et al. |
| 6,139,549 A | 10/2000 | Keller |
| 6,146,383 A | 11/2000 | Studer et al. |
| 6,149,653 A | 11/2000 | Deslauriers |
| 6,159,214 A | 12/2000 | Michelson |
| 6,179,838 B1 | 1/2001 | Fiz |
| 6,183,472 B1 | 2/2001 | Lutz |
| 6,187,005 B1 | 2/2001 | Brace et al. |
| 6,189,422 B1 | 2/2001 | Stihl |
| 6,200,322 B1 | 3/2001 | Branch et al. |
| 6,206,826 B1 | 3/2001 | Mathews et al. |
| 6,214,006 B1 | 4/2001 | Metz-Stavenhagen |
| 6,224,598 B1 | 5/2001 | Jackson |
| 6,224,603 B1 | 5/2001 | Marino |
| 6,235,028 B1 | 5/2001 | Brumfield et al. |
| 6,251,112 B1 | 6/2001 | Jackson |
| 6,261,287 B1 | 7/2001 | Metz-Stavenhagen |
| 6,280,442 B1 | 8/2001 | Barker et al. |
| 6,302,410 B1 | 10/2001 | Wentworth et al. |
| 6,302,888 B1 | 10/2001 | Mellinger et al. |
| 6,355,040 B1 | 3/2002 | Richelsoph et al. |
| 6,360,750 B1 | 3/2002 | Gerber et al. |
| 6,361,535 B2 | 3/2002 | Jackson |
| RE37,665 E | 4/2002 | Ralph et al. |
| 6,368,321 B1 | 4/2002 | Jackson |
| 6,402,749 B1 | 6/2002 | Ashman |
| 6,415,693 B1 | 7/2002 | Simon et al. |
| 6,440,113 B1 | 8/2002 | Brisebois et al. |
| 6,440,133 B1 | 8/2002 | Beale et al. |
| 6,475,218 B2 | 11/2002 | Gournay et al. |
| 6,485,491 B1 | 11/2002 | Farris et al. |
| 6,488,681 B2 | 12/2002 | Martin et al. |
| 6,488,682 B2 | 12/2002 | Kikuchi et al. |
| 6,512,958 B1 | 1/2003 | Swoyer et al. |
| 6,520,907 B1 | 2/2003 | Foley et al. |
| 6,530,926 B1 | 3/2003 | Davison |
| 6,530,929 B1 | 3/2003 | Justis et al. |
| 6,537,276 B2 | 3/2003 | Metz-Stavenhagen |
| 6,543,317 B1 | 4/2003 | Rinner et al. |
| 6,554,834 B1 | 4/2003 | Crozet et al. |
| 6,558,387 B2 | 5/2003 | Errico et al. |
| 6,565,565 B1 | 5/2003 | Yuan et al. |
| 6,579,291 B1 | 6/2003 | Keith et al. |
| 6,579,292 B2 | 6/2003 | Taylor |
| 6,610,065 B1 | 8/2003 | Branch et al. |
| 6,613,091 B1 | 9/2003 | Zdeblick et al. |
| 6,623,485 B2 | 9/2003 | Doubler et al. |
| 6,626,347 B2 | 9/2003 | Ng |
| 6,626,905 B1 | 9/2003 | Schmiel et al. |
| 6,626,906 B1 | 9/2003 | Young |
| 6,648,888 B1 | 11/2003 | Shluzas |
| 6,660,004 B2 | 12/2003 | Barker et al. |
| 6,669,729 B2 | 12/2003 | Chin |
| 6,673,074 B2 | 1/2004 | Shluzas |
| 6,676,661 B1 | 1/2004 | Martin et al. |
| 6,716,214 B1 | 4/2004 | Jackson |
| 6,719,758 B2 | 4/2004 | Beger et al. |
| 6,726,692 B2 | 4/2004 | Bette |
| 6,736,816 B2 | 5/2004 | Ritland |
| 6,743,231 B1 | 6/2004 | Gray et al. |
| 6,755,830 B2 | 6/2004 | Minfelde et al. |
| 6,780,186 B2 | 8/2004 | Errico et al. |
| 6,783,527 B2 | 8/2004 | Drewry et al. |
| 6,790,208 B2 | 9/2004 | Oribe et al. |

(56) References Cited

U.S. PATENT DOCUMENTS

| | | |
|---|---|---|
| 6,800,084 B2 | 10/2004 | Davison et al. |
| 6,821,277 B2 | 11/2004 | Teitelbaum |
| 6,827,722 B1 | 12/2004 | Schoenefeld |
| 6,835,196 B2 | 12/2004 | Biedermann et al. |
| 6,843,791 B2 | 1/2005 | Serhan |
| 6,849,064 B2 | 2/2005 | Hamada |
| 6,866,664 B2 | 3/2005 | Schaer et al. |
| 6,872,209 B2 | 3/2005 | Morrison |
| 6,929,606 B2 | 8/2005 | Ritland |
| 6,945,933 B2 | 9/2005 | Branch et al. |
| 7,008,422 B2 | 3/2006 | Foley et al. |
| 7,011,658 B2 | 3/2006 | Young |
| 7,011,660 B2 | 3/2006 | Sherman et al. |
| 7,018,379 B2 | 3/2006 | Drewry et al. |
| RE39,089 E | 5/2006 | Ralph et al. |
| 7,066,939 B2 | 6/2006 | Taylor |
| 7,083,621 B2 | 8/2006 | Shaolian et al. |
| 7,094,237 B2 | 8/2006 | Gradel et al. |
| 7,104,992 B2 | 9/2006 | Bailey |
| 7,128,743 B2 | 10/2006 | Metz-Stavenhagen |
| 7,160,300 B2 | 1/2007 | Jackson |
| 7,166,109 B2 | 1/2007 | Biedermann et al. |
| 7,179,225 B2 | 2/2007 | Shluzas et al. |
| 7,179,261 B2 | 2/2007 | Sicvol et al. |
| 7,186,255 B2 | 3/2007 | Baynham et al. |
| 7,188,626 B2 | 3/2007 | Foley et al. |
| 7,211,087 B2 | 5/2007 | Young |
| 7,250,052 B2 | 7/2007 | Landry et al. |
| 7,261,714 B2 | 8/2007 | Richelsoph |
| 7,270,665 B2 | 9/2007 | Morrison et al. |
| 7,282,064 B2 | 10/2007 | Chin |
| 7,303,562 B2 | 12/2007 | Cavagna et al. |
| 7,306,603 B2 | 12/2007 | Boehm et al. |
| 7,371,239 B2 | 5/2008 | Dec et al. |
| 7,390,298 B2 | 6/2008 | Chu |
| 7,422,597 B1 | 9/2008 | Alby |
| 7,442,597 B2 | 10/2008 | Tsui et al. |
| 7,455,685 B2 | 11/2008 | Justis |
| 7,462,182 B2 | 12/2008 | Lim |
| 7,465,306 B2 | 12/2008 | Pond et al. |
| 7,470,279 B2 | 12/2008 | Jackson |
| 7,476,240 B2 | 1/2009 | Raymond et al. |
| 7,491,207 B2 | 2/2009 | Keyer et al. |
| 7,491,208 B2 | 2/2009 | Pond et al. |
| 7,491,218 B2 | 2/2009 | Landry et al. |
| 7,497,869 B2 | 3/2009 | Justis |
| 7,520,879 B2 | 4/2009 | Justis et al. |
| 7,527,638 B2 | 5/2009 | Anderson et al. |
| 7,547,318 B2 | 6/2009 | Birkmeyer et al. |
| 7,563,264 B2 | 7/2009 | Landry et al. |
| 7,572,276 B2 | 8/2009 | Lim et al. |
| 7,597,694 B2 | 10/2009 | Lim et al. |
| 7,608,081 B2 | 10/2009 | Abdelgany |
| 7,608,096 B2 | 10/2009 | Foley et al. |
| 7,618,424 B2 | 11/2009 | Wilcox et al. |
| 7,621,918 B2 | 11/2009 | Jackson |
| 7,648,522 B2 | 1/2010 | David |
| 7,651,502 B2 | 1/2010 | Jackson |
| 7,651,516 B2 | 1/2010 | Petit et al. |
| 7,666,189 B2 | 2/2010 | Gerber et al. |
| 7,678,112 B2 | 3/2010 | Rezach |
| 7,678,136 B2 | 3/2010 | Doubler et al. |
| 7,686,809 B2 | 3/2010 | Triplett et al. |
| 7,691,132 B2 | 4/2010 | Landry et al. |
| 7,704,270 B2 | 4/2010 | De Coninck |
| 7,708,763 B2 | 5/2010 | Selover et al. |
| 7,717,944 B2 | 5/2010 | Foley et al. |
| 7,722,645 B2 | 5/2010 | Bryan |
| 7,744,635 B2 | 6/2010 | Sweeney et al. |
| 7,753,940 B2 | 7/2010 | Veldman et al. |
| 7,758,584 B2 | 7/2010 | Bankoski et al. |
| 7,763,047 B2 | 7/2010 | Ritland |
| 7,763,054 B2 | 7/2010 | Clement et al. |
| 7,763,055 B2 | 7/2010 | Foley |
| 7,776,040 B2 | 8/2010 | Markworth et al. |
| 7,776,051 B2 | 8/2010 | Colleran et al. |
| 7,789,897 B2 | 9/2010 | Sanders |
| 7,799,059 B2 | 9/2010 | Kramer et al. |
| 7,811,288 B2 | 10/2010 | Jones et al. |
| 7,815,664 B2 | 10/2010 | Sherman et al. |
| 7,819,902 B2 | 10/2010 | Abdelgany et al. |
| 7,824,411 B2 | 11/2010 | Varieur et al. |
| 7,824,413 B2 | 11/2010 | Varieur et al. |
| 7,837,715 B2 | 11/2010 | Petit et al. |
| 7,842,044 B2 | 11/2010 | Runco et al. |
| 7,842,073 B2 | 11/2010 | Richelsoph et al. |
| 7,850,715 B2 | 12/2010 | Banouskou et al. |
| 7,850,716 B2 | 12/2010 | Taylor |
| 7,850,719 B2 | 12/2010 | Gournay et al. |
| 7,854,751 B2 | 12/2010 | Sicvol et al. |
| 7,862,587 B2 | 1/2011 | Jackson |
| 7,862,595 B2 | 1/2011 | Foley et al. |
| 7,867,259 B2 | 1/2011 | Foley et al. |
| 7,887,539 B2 | 2/2011 | Dunbar et al. |
| 7,896,902 B2 | 3/2011 | Jeon et al. |
| 7,914,558 B2 | 3/2011 | Landry et al. |
| 7,918,792 B2 | 4/2011 | Drzyzga et al. |
| 7,931,677 B2 | 4/2011 | Abdelgany |
| 7,955,355 B2 | 6/2011 | Chin |
| 7,955,363 B2 | 6/2011 | Richelsoph |
| 7,976,569 B2 | 7/2011 | Justis |
| 7,985,242 B2 | 7/2011 | Forton et al. |
| 8,002,798 B2 | 8/2011 | Chin et al. |
| 8,021,398 B2 | 9/2011 | Sweeney et al. |
| 8,029,546 B2 | 10/2011 | Capote et al. |
| 8,034,084 B2 | 10/2011 | Landry et al. |
| 8,043,343 B2 | 10/2011 | Miller et al. |
| 8,048,129 B2 * | 11/2011 | Forton ............... A61B 17/7085 606/279 |
| 8,052,720 B2 | 11/2011 | Kuester et al. |
| 8,066,739 B2 | 11/2011 | Jackson |
| 8,075,592 B2 | 12/2011 | Landry et al. |
| 8,088,152 B2 | 1/2012 | Schumacher |
| 8,092,494 B2 | 1/2012 | Butler et al. |
| 8,096,996 B2 | 1/2012 | Gutierrez et al. |
| 8,097,026 B2 | 1/2012 | Gorek |
| 8,097,027 B2 | 1/2012 | Lim et al. |
| 8,100,828 B2 | 1/2012 | Frey et al. |
| 8,100,913 B2 | 1/2012 | Abdelgany |
| 8,100,915 B2 | 1/2012 | Jackson |
| 8,100,951 B2 | 1/2012 | Justis et al. |
| 8,105,361 B2 | 1/2012 | Anderson et al. |
| 8,118,737 B2 | 2/2012 | Perez-Cruet et al. |
| 8,123,751 B2 | 2/2012 | Shluzas |
| 8,128,665 B2 | 3/2012 | Banouskou et al. |
| 8,152,810 B2 | 4/2012 | Jackson |
| 8,172,855 B2 | 5/2012 | Abdou |
| 8,177,817 B2 | 5/2012 | Fallin |
| 8,221,472 B2 | 7/2012 | Peterson et al. |
| 8,262,662 B2 | 9/2012 | Beardsley et al. |
| 8,262,702 B2 | 9/2012 | Giger et al. |
| 8,287,546 B2 | 10/2012 | King et al. |
| 8,292,892 B2 | 10/2012 | Jackson |
| 8,317,796 B2 | 11/2012 | Stihl et al. |
| 8,357,184 B2 | 1/2013 | Woolley et al. |
| 8,460,308 B2 | 6/2013 | Marino et al. |
| 8,469,960 B2 | 6/2013 | Hutton et al. |
| 8,480,713 B2 | 7/2013 | Rezach |
| 8,518,082 B2 | 8/2013 | Sicvol et al. |
| 8,535,318 B2 | 9/2013 | Peterson et al. |
| 8,545,505 B2 | 10/2013 | Sandstrom et al. |
| 8,585,741 B2 | 11/2013 | Gabelberger et al. |
| 8,608,746 B2 | 12/2013 | Kolb et al. |
| 8,617,218 B2 | 12/2013 | Justis et al. |
| 8,679,129 B2 | 3/2014 | Sorrenti et al. |
| 8,721,691 B2 | 5/2014 | Hua |
| 8,747,407 B2 | 6/2014 | Gorek |
| RE45,338 E | 1/2015 | Chin et al. |
| 9,101,416 B2 | 8/2015 | Dunbar et al. |
| RE45,676 E | 9/2015 | Chin et al. |
| 9,265,548 B2 | 2/2016 | Jones et al. |
| 9,314,274 B2 | 4/2016 | Amstutz et al. |
| 9,364,265 B2 | 6/2016 | Ramsay et al. |
| 9,402,663 B2 | 8/2016 | Peterson et al. |

(56) References Cited

U.S. PATENT DOCUMENTS

| | | |
|---|---|---|
| 9,808,281 B2 | 11/2017 | Solitario |
| 9,918,751 B2 | 3/2018 | Jackson |
| 2002/0020255 A1 | 2/2002 | Simon et al. |
| 2002/0035367 A1 | 3/2002 | Ritland |
| 2002/0107519 A1 | 8/2002 | Dixon et al. |
| 2002/0193802 A1 | 12/2002 | Zdeblick et al. |
| 2003/0040752 A1 | 2/2003 | Kitchens |
| 2003/0073998 A1 | 4/2003 | Pagliuca et al. |
| 2003/0100896 A1 | 5/2003 | Biedermann et al. |
| 2003/0115180 A1 | 6/2003 | Eves et al. |
| 2003/0135220 A1 | 7/2003 | Cauthen |
| 2003/0149341 A1 | 8/2003 | Clifton |
| 2003/0149438 A1 | 8/2003 | Nichols et al. |
| 2003/0191371 A1 | 10/2003 | Smith et al. |
| 2003/0199872 A1 | 10/2003 | Markworth et al. |
| 2003/0208203 A1 | 11/2003 | Lim et al. |
| 2003/0216768 A1 | 11/2003 | Gitis et al. |
| 2003/0225408 A1 | 12/2003 | Nichols et al. |
| 2003/0236447 A1 | 12/2003 | Ritland |
| 2004/0002629 A1 | 1/2004 | Branch et al. |
| 2004/0024398 A1 | 2/2004 | Hovda et al. |
| 2004/0034351 A1 | 2/2004 | Sherman et al. |
| 2004/0039384 A1 | 2/2004 | Boehm et al. |
| 2004/0092930 A1 | 5/2004 | Petit et al. |
| 2004/0138662 A1 | 7/2004 | Landry et al. |
| 2004/0143265 A1 | 7/2004 | Landry et al. |
| 2004/0147928 A1 | 7/2004 | Landry et al. |
| 2004/0147937 A1 | 7/2004 | Dunbar et al. |
| 2004/0153068 A1 | 8/2004 | Janowski et al. |
| 2004/0172022 A1 | 9/2004 | Landry et al. |
| 2004/0176763 A1 | 9/2004 | Foley et al. |
| 2004/0215190 A1 | 10/2004 | Nguyen et al. |
| 2004/0254574 A1 | 12/2004 | Morrison et al. |
| 2004/0267275 A1 | 12/2004 | Cournoyer et al. |
| 2005/0004593 A1 | 1/2005 | Simonson |
| 2005/0010214 A1 | 1/2005 | Tassin |
| 2005/0010220 A1 | 1/2005 | Casutt et al. |
| 2005/0021031 A1 | 1/2005 | Foley et al. |
| 2005/0021040 A1 | 1/2005 | Bertagnoli |
| 2005/0036244 A1 | 2/2005 | Carey et al. |
| 2005/0038432 A1 | 2/2005 | Shaolian et al. |
| 2005/0038433 A1 | 2/2005 | Young |
| 2005/0065517 A1 | 3/2005 | Chin |
| 2005/0065518 A1 | 3/2005 | Michelson |
| 2005/0070765 A1 | 3/2005 | Abdelgany et al. |
| 2005/0070901 A1 | 3/2005 | David |
| 2005/0074445 A1 | 4/2005 | Papas et al. |
| 2005/0075644 A1 | 4/2005 | Dipoto et al. |
| 2005/0080418 A1 | 4/2005 | Simonson et al. |
| 2005/0085813 A1 | 4/2005 | Spitler et al. |
| 2005/0090824 A1 | 4/2005 | Shluzas et al. |
| 2005/0096654 A1 | 5/2005 | Lin |
| 2005/0131408 A1 | 6/2005 | Sicvol et al. |
| 2005/0131419 A1 | 6/2005 | Mccord et al. |
| 2005/0131420 A1 | 6/2005 | Techiera et al. |
| 2005/0131421 A1 | 6/2005 | Anderson et al. |
| 2005/0131422 A1 | 6/2005 | Anderson et al. |
| 2005/0149036 A1 | 7/2005 | Varieur et al. |
| 2005/0149053 A1 | 7/2005 | Varieur et al. |
| 2005/0154389 A1 | 7/2005 | Selover et al. |
| 2005/0159650 A1 | 7/2005 | Raymond et al. |
| 2005/0171540 A1 | 8/2005 | Lim et al. |
| 2005/0182410 A1 | 8/2005 | Jackson |
| 2005/0192570 A1 | 9/2005 | Jackson |
| 2005/0192579 A1 | 9/2005 | Jackson |
| 2005/0192589 A1 | 9/2005 | Raymond et al. |
| 2005/0203532 A1 | 9/2005 | Ferguson et al. |
| 2005/0215999 A1 | 9/2005 | Birkmeyer et al. |
| 2005/0228380 A1 | 10/2005 | Moore et al. |
| 2005/0228382 A1 | 10/2005 | Richelsoph et al. |
| 2005/0228400 A1 | 10/2005 | Chao et al. |
| 2005/0234449 A1 | 10/2005 | Aferzon |
| 2005/0240181 A1 | 10/2005 | Boomer et al. |
| 2005/0273167 A1 | 12/2005 | Triplett et al. |
| 2005/0277934 A1 | 12/2005 | Vardiman |
| 2006/0005914 A1 | 1/2006 | Blum et al. |
| 2006/0009780 A1 | 1/2006 | Foley et al. |
| 2006/0025768 A1 | 2/2006 | Iott et al. |
| 2006/0036244 A1 | 2/2006 | Spitler et al. |
| 2006/0036252 A1 | 2/2006 | Baynham et al. |
| 2006/0036255 A1 | 2/2006 | Pond et al. |
| 2006/0036260 A1 | 2/2006 | Runco et al. |
| 2006/0069391 A1 | 3/2006 | Jackson |
| 2006/0074418 A1 | 4/2006 | Jackson |
| 2006/0074445 A1 | 4/2006 | Gerber et al. |
| 2006/0079894 A1 | 4/2006 | Colleran et al. |
| 2006/0079909 A1 | 4/2006 | Runco et al. |
| 2006/0084993 A1 | 4/2006 | Landry et al. |
| 2006/0095035 A1 | 5/2006 | Jones et al. |
| 2006/0106380 A1 | 5/2006 | Colleran et al. |
| 2006/0106394 A1 | 5/2006 | Colleran |
| 2006/0111712 A1 | 5/2006 | Jackson |
| 2006/0111713 A1 | 5/2006 | Jackson |
| 2006/0111714 A1 | 5/2006 | Foley |
| 2006/0111715 A1 | 5/2006 | Jackson |
| 2006/0122597 A1 | 6/2006 | Jones et al. |
| 2006/0136380 A1 | 6/2006 | Purcell |
| 2006/0142716 A1 | 6/2006 | Long et al. |
| 2006/0142761 A1 | 6/2006 | Landry et al. |
| 2006/0167454 A1 | 7/2006 | Ludwig et al. |
| 2006/0167455 A1 | 7/2006 | Clement et al. |
| 2006/0173454 A1 | 8/2006 | Spitler et al. |
| 2006/0184172 A1 | 8/2006 | Michelson |
| 2006/0184178 A1 | 8/2006 | Jackson |
| 2006/0200135 A1 | 9/2006 | Sherman et al. |
| 2006/0200186 A1 | 9/2006 | Marchek et al. |
| 2006/0206114 A1 | 9/2006 | Ensign et al. |
| 2006/0229614 A1 | 10/2006 | Foley et al. |
| 2006/0241596 A1 | 10/2006 | Rezach |
| 2006/0241601 A1 | 10/2006 | Trautwein et al. |
| 2006/0241649 A1 | 10/2006 | Vasta et al. |
| 2006/0247624 A1 | 11/2006 | Banouskou et al. |
| 2006/0247630 A1 | 11/2006 | Iott et al. |
| 2006/0247658 A1 | 11/2006 | Pond et al. |
| 2006/0253118 A1 | 11/2006 | Bailey |
| 2006/0264942 A1 | 11/2006 | Lim et al. |
| 2006/0264962 A1 | 11/2006 | Chin et al. |
| 2006/0276803 A1 | 12/2006 | Salerni |
| 2006/0293678 A1 | 12/2006 | Davison et al. |
| 2006/0293680 A1 | 12/2006 | Jackson |
| 2006/0293693 A1 | 12/2006 | Farr et al. |
| 2007/0016188 A1 | 1/2007 | Boehm et al. |
| 2007/0016198 A1 | 1/2007 | Boehm et al. |
| 2007/0016199 A1 | 1/2007 | Boehm et al. |
| 2007/0016200 A1 | 1/2007 | Jackson |
| 2007/0025132 A1 | 2/2007 | Liaw |
| 2007/0032162 A1 | 2/2007 | Jackson |
| 2007/0073294 A1* | 3/2007 | Chin ............... A61B 17/7091 606/86 A |
| 2007/0083210 A1 | 4/2007 | Hestad et al. |
| 2007/0106123 A1 | 5/2007 | Gorek et al. |
| 2007/0129731 A1 | 6/2007 | Sicvol et al. |
| 2007/0135817 A1 | 6/2007 | Ensign |
| 2007/0161987 A1 | 7/2007 | Capote et al. |
| 2007/0161998 A1 | 7/2007 | Whipple |
| 2007/0162046 A1 | 7/2007 | Vandewalle |
| 2007/0167946 A1 | 7/2007 | Triplett et al. |
| 2007/0167954 A1 | 7/2007 | Sicvol et al. |
| 2007/0173745 A1 | 7/2007 | Diederich et al. |
| 2007/0185491 A1 | 8/2007 | Foley et al. |
| 2007/0198015 A1 | 8/2007 | Foley et al. |
| 2007/0233067 A1 | 10/2007 | Taylor |
| 2007/0233079 A1 | 10/2007 | Fallin et al. |
| 2007/0238335 A1 | 10/2007 | Veldman et al. |
| 2007/0260125 A1 | 11/2007 | Strauss et al. |
| 2007/0270842 A1 | 11/2007 | Bankoski et al. |
| 2007/0276803 A1 | 11/2007 | Shakib et al. |
| 2008/0005174 A1 | 1/2008 | Stephenson |
| 2008/0009864 A1 | 1/2008 | Forton et al. |
| 2008/0039838 A1 | 2/2008 | Landry et al. |
| 2008/0045957 A1 | 2/2008 | Landry et al. |
| 2008/0051794 A1 | 2/2008 | Dec et al. |
| 2008/0051897 A1 | 2/2008 | Lopez et al. |
| 2008/0077139 A1 | 3/2008 | Landry et al. |

(56) References Cited

U.S. PATENT DOCUMENTS

| | | |
|---|---|---|
| 2008/0077155 A1 | 3/2008 | Diederich et al. |
| 2008/0081951 A1 | 4/2008 | Frasier et al. |
| 2008/0086132 A1 | 4/2008 | Biedermann et al. |
| 2008/0091213 A1* | 4/2008 | Jackson ............ A61B 17/7082 606/99 |
| 2008/0140120 A1 | 6/2008 | Hestad et al. |
| 2008/0140132 A1 | 6/2008 | Perez-Cruet |
| 2008/0154278 A1 | 6/2008 | Abdelgany |
| 2008/0167688 A1 | 7/2008 | Fauth et al. |
| 2008/0177270 A1 | 7/2008 | Sorrenti et al. |
| 2008/0183044 A1 | 7/2008 | Colleran et al. |
| 2008/0255567 A1 | 10/2008 | Accordino |
| 2008/0262318 A1 | 10/2008 | Gorek et al. |
| 2008/0288005 A1 | 11/2008 | Jackson |
| 2008/0294198 A1 | 11/2008 | Jackson |
| 2008/0294202 A1 | 11/2008 | Peterson et al. |
| 2008/0300638 A1 | 12/2008 | Beardsley et al. |
| 2009/0005814 A1 | 1/2009 | Miller et al. |
| 2009/0088604 A1 | 4/2009 | Lowry et al. |
| 2009/0093684 A1 | 4/2009 | Schorer |
| 2009/0099605 A1 | 4/2009 | Fallin et al. |
| 2009/0131755 A1 | 5/2009 | White et al. |
| 2009/0138056 A1 | 5/2009 | Anderson et al. |
| 2009/0163924 A1 | 6/2009 | Justis |
| 2009/0171391 A1 | 7/2009 | Hutton et al. |
| 2009/0228052 A1 | 9/2009 | Beardsley et al. |
| 2009/0228055 A1 | 9/2009 | Jackson |
| 2009/0228056 A1 | 9/2009 | Jackson |
| 2009/0264926 A1 | 10/2009 | Taylor et al. |
| 2009/0270916 A1 | 10/2009 | Ramsay et al. |
| 2009/0287253 A1 | 11/2009 | Felix et al. |
| 2009/0318972 A1 | 12/2009 | Jackson |
| 2009/0326585 A1 | 12/2009 | Baccelli et al. |
| 2010/0024487 A1 | 2/2010 | Khoo et al. |
| 2010/0030283 A1 | 2/2010 | King et al. |
| 2010/0036443 A1 | 2/2010 | Hutton et al. |
| 2010/0049253 A1 | 2/2010 | Miller |
| 2010/0063546 A1 | 3/2010 | Miller et al. |
| 2010/0094346 A1 | 4/2010 | Matityahu |
| 2010/0114174 A1 | 5/2010 | Jones et al. |
| 2010/0114179 A1 | 5/2010 | Moore et al. |
| 2010/0131016 A1 | 5/2010 | Gerber et al. |
| 2010/0168796 A1 | 7/2010 | Eliasen et al. |
| 2010/0174325 A1 | 7/2010 | Won et al. |
| 2010/0185248 A1 | 7/2010 | Barry et al. |
| 2010/0198272 A1 | 8/2010 | Keyer et al. |
| 2010/0241171 A1 | 9/2010 | Clement et al. |
| 2010/0268279 A1 | 10/2010 | Gabelberger et al. |
| 2010/0268284 A1 | 10/2010 | Bankoski et al. |
| 2010/0274252 A1 | 10/2010 | Bottomley et al. |
| 2010/0331849 A1 | 12/2010 | Riesinger et al. |
| 2011/0054537 A1 | 3/2011 | Miller et al. |
| 2011/0130634 A1 | 6/2011 | Solitario et al. |
| 2011/0166606 A1 | 7/2011 | Stihl et al. |
| 2011/0184465 A1 | 7/2011 | Boehm |
| 2011/0184469 A1 | 7/2011 | Ballard et al. |
| 2011/0263945 A1 | 10/2011 | Peterson et al. |
| 2012/0089191 A1 | 4/2012 | Altarac et al. |
| 2012/0290012 A1 | 11/2012 | Rutledge |
| 2012/0303062 A1 | 11/2012 | Amstutz et al. |
| 2013/0253598 A1 | 9/2013 | Jackson |
| 2013/0274804 A1 | 10/2013 | Hutton et al. |
| 2013/0304130 A1* | 11/2013 | Jackson ............ A61B 17/7008 606/278 |
| 2013/0331892 A1 | 12/2013 | Peterson et al. |
| 2014/0012321 A1 | 1/2014 | Hutton et al. |
| 2014/0074171 A1 | 3/2014 | Hutton et al. |
| 2014/0114360 A1 | 4/2014 | Gephart et al. |
| 2016/0199100 A1 | 7/2016 | Amstutz et al. |
| 2018/0014863 A1 | 1/2018 | Biester et al. |

FOREIGN PATENT DOCUMENTS

| | | |
|---|---|---|
| CN | 1913836 A | 2/2007 |
| DE | 9215561.8 U1 | 1/1993 |
| DE | 4238339 A1 | 5/1994 |
| DE | 19726754 A1 | 2/1999 |
| DE | 10027988 A1 | 1/2002 |
| EP | 0528177 A2 | 2/1993 |
| EP | 0558883 A1 | 9/1993 |
| EP | 0483242 B1 | 5/1995 |
| EP | 0836835 A2 | 4/1998 |
| EP | 0885598 A2 | 12/1998 |
| EP | 0947174 A2 | 10/1999 |
| EP | 0938872 B1 | 7/2002 |
| EP | 0746255 B1 | 9/2002 |
| EP | 0814716 B1 | 7/2003 |
| EP | 0981301 B1 | 8/2003 |
| EP | 0934027 B1 | 12/2003 |
| EP | 0814713 B1 | 2/2004 |
| EP | 1087711 B1 | 5/2004 |
| EP | 0934028 B1 | 6/2004 |
| EP | 1196102 B1 | 9/2004 |
| EP | 1459215 A2 | 9/2004 |
| EP | 1214006 B1 | 10/2005 |
| EP | 1316295 B1 | 10/2005 |
| EP | 1330196 B1 | 10/2005 |
| EP | 1119304 B1 | 12/2005 |
| EP | 1317215 B1 | 12/2005 |
| EP | 1642542 A2 | 4/2006 |
| EP | 0986338 B1 | 7/2006 |
| EP | 1248573 B1 | 8/2006 |
| EP | 1392190 B1 | 8/2006 |
| EP | 1708630 A1 | 10/2006 |
| EP | 1635722 B1 | 6/2008 |
| FR | 2757761 A1 | 7/1998 |
| JP | 11-076247 | 3/1999 |
| JP | 2000-032359 A | 1/2000 |
| JP | 2001-507259 A | 6/2001 |
| JP | 2004-512134 A | 4/2004 |
| JP | 2004-516040 A | 6/2004 |
| JP | 2006-504505 A | 2/2006 |
| JP | 2007-532258 A | 11/2007 |
| JP | 2010-533547 A | 10/2010 |
| JP | 2012-501809 | 1/2012 |
| JP | 2012-050189 A | 3/2012 |
| KR | 10-2009-0005316 A | 1/2009 |
| WO | 91/01115 A1 | 2/1991 |
| WO | 95/13754 A1 | 5/1995 |
| WO | 95/14437 | 6/1995 |
| WO | 96/27340 A1 | 9/1996 |
| WO | 96/28104 A1 | 9/1996 |
| WO | 98/12976 A1 | 4/1998 |
| WO | 98/12977 A1 | 4/1998 |
| WO | 98/34554 A1 | 8/1998 |
| WO | 99/65415 A1 | 12/1999 |
| WO | 01/06939 A1 | 2/2001 |
| WO | 01/15612 A1 | 3/2001 |
| WO | 01/52758 A1 | 7/2001 |
| WO | 02/02022 A1 | 1/2002 |
| WO | 02/22030 A2 | 3/2002 |
| WO | 02/36026 A2 | 5/2002 |
| WO | 02/94114 A1 | 11/2002 |
| WO | 03/52634 A2 | 6/2003 |
| WO | 00/19923 A1 | 4/2004 |
| WO | 2004/041100 A1 | 5/2004 |
| WO | 04/58082 | 7/2004 |
| WO | 2005/020829 A1 | 3/2005 |
| WO | 2005/058141 A2 | 6/2005 |
| WO | 05/60534 A2 | 7/2005 |
| WO | 2005/072632 A1 | 8/2005 |
| WO | 2005/104970 A1 | 11/2005 |
| WO | 2006/042188 A2 | 4/2006 |
| WO | 06/60430 A1 | 6/2006 |
| WO | 2006/116305 A1 | 11/2006 |
| WO | 2006/116662 A1 | 11/2006 |
| WO | 2007/022790 A1 | 3/2007 |
| WO | 2007/025132 A2 | 3/2007 |
| WO | 2007/038350 A2 | 4/2007 |
| WO | 2007/067443 A2 | 6/2007 |

(56) References Cited

FOREIGN PATENT DOCUMENTS

| WO | 2007/070757 A2 | 6/2007 |
|---|---|---|
| WO | 2007/117366 A2 | 10/2007 |
| WO | 2007/121271 A2 | 10/2007 |
| WO | 2007/146833 A2 | 12/2007 |
| WO | 2008/014477 A1 | 1/2008 |
| WO | 2008/022268 A2 | 2/2008 |
| WO | 2009/011929 A1 | 1/2009 |
| WO | 2009/014540 A1 | 1/2009 |
| WO | 2009/015100 A3 | 4/2009 |
| WO | 2009/055026 A1 | 4/2009 |
| WO | 2009/133539 A1 | 11/2009 |
| WO | 2010/030916 A2 | 3/2010 |
| WO | 2010/103198 A1 | 9/2010 |
| WO | 2010/150140 A1 | 12/2010 |
| WO | 2011/012690 A1 | 2/2011 |

OTHER PUBLICATIONS

Wiltse, et al., New Uses and Refinements of the Paraspinal Approach to the Lumbar Sine, 12 pages, Nov. 16, 1967.
Viper 2 System Guide, DePuy Spine, 2011, 60 pages.
Turner, "A new, radially expanding access system for laparoscopic procedures versus conventional cannulas", The Journal of the American Association of Gynecologic Laparoscopists, Aug. 1996, 3(4), 609-615.
Thongtrangan, et al. "Minimimally Invasive Spinal Surgery: A Historical Perspective"; Neurosurg Focus, pp. 1-10, vol. 16, Jan. 2004.
Synthes Spine, "USS Fracture System: Technique Guide", 2001, 20 pages.
Muller et al., "Techniques and Applications : A Keyhole Approach for Endoscopically assisted Pedicle Screw Fixation in Lumbar Spine Inability", Jul. 2000 Neurosurgery, 47(1), 11 pages.
Muller et al., "A keyhole approach for endoscopically assisted pedicle screw fixation in lumbar spine instability (techniques and applications)", Department of Neurosurgery, 1999, 18 pages.
Matrix Spine System—Deformity Technique Guide, "A Posterior Pedicle Screw, Hook, and Rod Fixation System," Synthes, copyrights 2010, 75 pages.
Kambin, "The role of minimally invasive surgery in spinal disorder", Advances in Operative Orhtopaedics, 1995, 147-171.
International Patent Application No. PCT/US2007/066469: International Search Report dated Aug. 1, 2008, 6 pages.
Hilton, Jr. et al., Medtronic Sofamor Danek, "Metrx microdiscectomy surgical technique", Neurological Surgery, 2000, 19 pages.
Harms; Moss Miami, "Polyaxial Reduction Screw; Surgical Technique", DePuy AcroMed; 13 pages, 1998.
Foley, Medtronic Sofamor Danek, "CD horizon SEXTANT rod insertion system surgical technique", Department of Neurosurgery, Un. of Tenn., 2002, 30 pages.
Constenation CP System, "A Minimally Invasive System for Use with Cannulated Pangea", Technique Guide; Synthes Spinem, 41 pages, 2008.
Branch, et al., "TANGENT Posterior Impacted Instrument Set Technique", Medtronic Sofamor Danek, 16 pages, 2000.
Atavi Atraumatic Spine Fusion System, "Endoscopic Posterolateral Fusion", 2001, 10 pages.
Aperture Trademark, "Spinal Access System", DePuy AcroMed, 2003, 6 pages.

\* cited by examiner

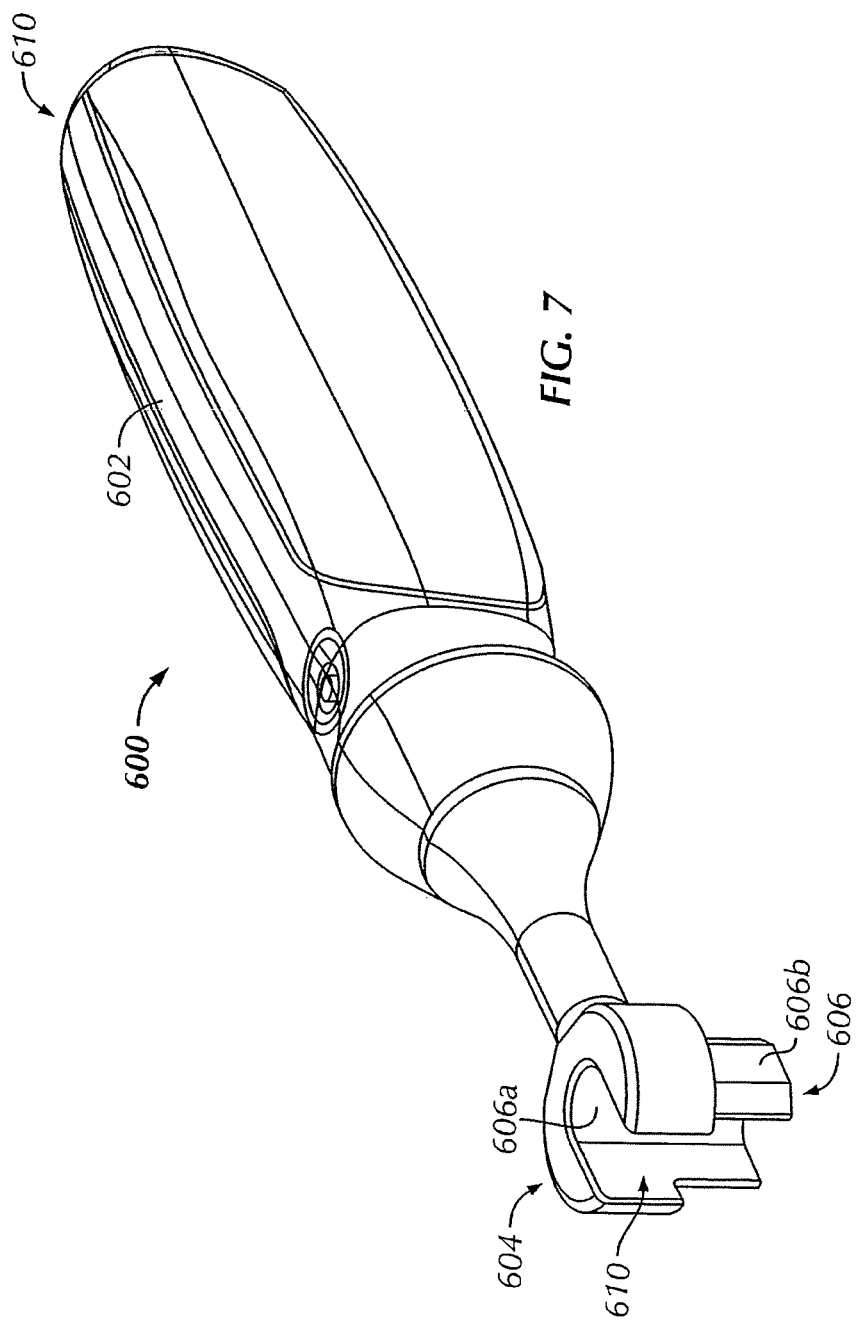

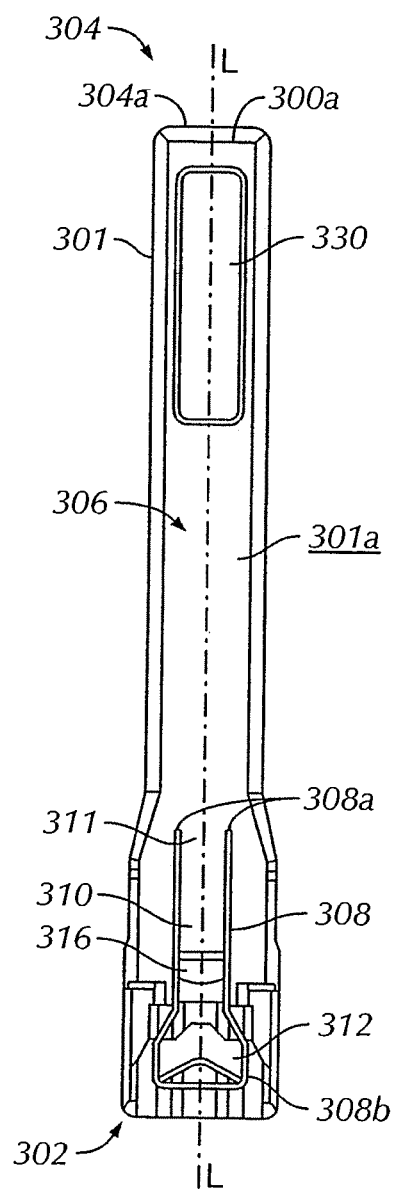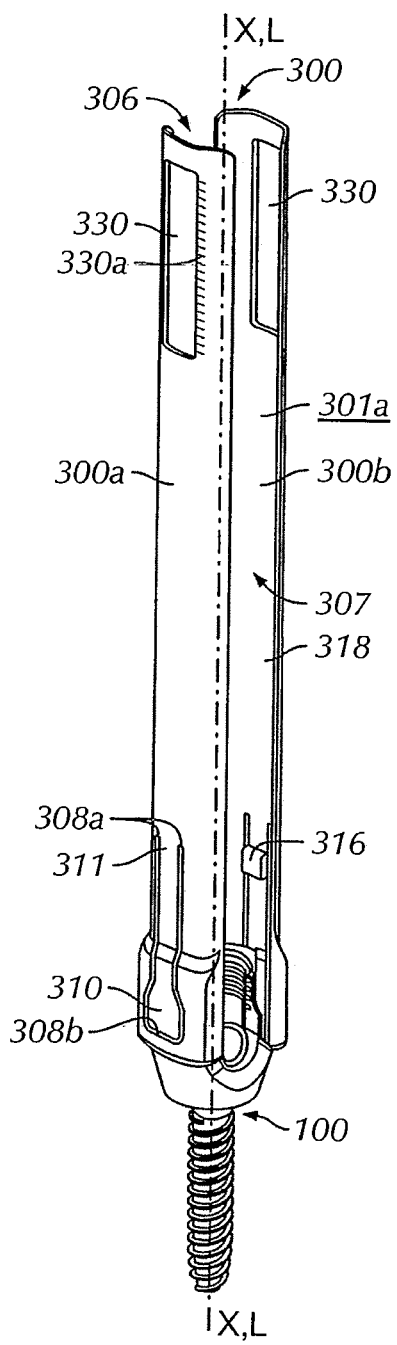
FIG. 16
FIG. 17

MINIMALLY INVASIVE INSTRUMENT SET, DEVICES, AND RELATED METHODS

CROSS REFERENCE TO RELATED APPLICATIONS

This application is a continuation of U.S. application Ser. No. 15/202,959, filed Jul. 6, 2016, which is a continuation application of U.S. application Ser. No. 13/965,764, filed Aug. 13, 2013, which is a divisional of U.S. application Ser. No. 12/766,393, filed Apr. 23, 2010, now U.S. Pat. No. 8,535,318 issued Sep. 17, 2013, the contents of each of which are hereby incorporated by reference as if set forth in their entirety herein.

BACKGROUND

Retractors provide a surgeon with an access portal or pathway to a surgical site, for example during spine surgeries such as discectomies, laminectomies, facecetomies, interbody fusions, pedicle screw fixation and similar procedures. Traditional spine surgeries were conducted utilizing an open procedure resulting in a relatively large incision, disruption or resection of significant soft tissue and long recovery times for patients. Minimally invasive techniques have become increasingly popular, particularly for spine surgeries, wherein relatively small incisions and surgical pathways are utilized to perform surgical procedures on a patient, generally resulting in a smaller incision or several relatively small incisions, less retraction and resection of soft tissue and shorter recovery times for patients in comparison to open procedures. Minimally invasive procedures are, in certain circumstances, able to obtain comparable or improved long term surgical outcomes in comparison to open procedures and may provide short term benefits including reduced post-operative pain, reduced use of post-operative narcotics, reduced tissue disruption, thereby permitting reduced scar tissue and potential benefits if a revision is necessary, reduced blood loss, accelerated recovery time, shorter hospital stays and cosmetically appealing smaller incisions. However, the smaller incision or incisions diminish the line-of-sight for a surgeon to directly view a surgical site, because patient soft tissue often limits a surgeon's ability to view the surgical site.

A common procedure in spine surgeries involves fixing screws to several vertebra and securing the screws and vertebra relative to each other with a rod. Such spinal constructs are typically implanted by mounting enclosed or substantially enclosed cannulae or sleeves to the screws such that the enclosed cannulae or sleeves create a surgical pathway through soft tissue and provide access for the surgeon to the surgical site. Minimally invasive spine instruments utilized for such procedures can be difficult to assemble, limit a surgeons ability to view the surgical site, are bulky and extend a significant distance out of a patient's skin, may detach from the screws during the procedure, are complicated to operate involving many steps, result in procedures involving removal and replacement of multiple instruments, inhibit imaging utilizing a C-arm or Fluoroscope as a result of their size and material composition and may be difficult to detach from the screws at the conclusion of the procedure. In addition, current minimally invasive fixation of screws and placement of rods in spine surgery often result in undesirable levels of trauma to a patient's soft tissue in and around the surgical site, along the surgical pathway and proximate the incision. Once assembled for rod insertion, these conventional minimally invasive systems are typically locked into a predetermined position and inhibit a surgeon's options in adapting their surgical technique to a particular patient's anatomy or in adapting the instruments to implant the components in a manner that would benefit the patient.

Certain conventional, minimally invasive spine instrumentation for the placement of pedicle screws and rods is bulky and complicated to utilize with multiple tool exchanges and complicated steps in mounting, removing, aligning and otherwise manipulating the bulky instrumentation to secure screws in the vertebrae and fix the rod to the implanted screws. A surgeon is often unable to directly visualize the surgical site, the screws and/or the rods once they are implanted in a patient, because of the bulky instruments and the relatively small size of the surgical incisions. Accordingly, a surgeon often relies on fluoroscopy to verify that screws and rods are properly placed in a patient and are securely fixed together. Accurate intra-operative visualization of the implant construct can be difficult for a spine surgeon to verify with fluoroscopy because the relatively bulky metallic instruments attached to the construct are radio-opaque.

In addition, the complicated procedures and instrumentation utilized with certain minimally invasive spine surgeries often require removal and replacement of different instruments through the enclosed cannulas or sleeves, thereby fatiguing a surgeon and extending the time that a patient is in surgery and subjected to anesthesia. Further, complicated procedures and instrumentation can lead to surgical delays, particularly for newly trained or novice surgical staff and surgeons when deciphering the complicated procedures and instrumentation. For example, certain counter-torque tools have been specially designed to fit within or onto minimally invasive spinal cannulas or sleeves that may result in several tool exchanges to tighten locking caps onto spinal rods. Further, the grasping handle of the counter-torque tool of conventional minimally invasive spine surgical sets can impede the surgeons visibility or prevent the use of other instruments during the procedure. Further, locking caps are often introduced through and into the substantially enclosed sleeves or cannulae of conventional systems with a screwdriver that must be removed from the sleeve or cannula several times during the procedure to introduce instruments such as the counter-torque sleeve, a distractor, a compressor or similar instruments. The screwdriver typically a self-retaining tip that has a limited ability to retain the locking cap if the sides of the sleeve or cannula are impacted with the locking cap, resulting in the locking cap becoming detached and falling into the incision, thereby requiring removal of the screwdriver and retrieval of the locking cap through the sleeve or cannula or through one of the minimal incisions. Accordingly, it would be desirable to construct a minimally invasive spine instrument set with a counter-torque tool that is relatively easy to secure to a screw for tightening of a locking cap and is relatively easy to remove and replace so that the instrument is only in the theatre when necessary for tightening purposes. It is also desirable to design and construct an instrument set that permits insertion of the locking cap into a minimally invasive incision utilizing a more robust retaining feature than the self-retaining tip of a screwdriver.

Further, conventional minimally invasive instrument sets often have an unwieldy number of excess protruding parts proximate the incision, often for the purpose of fixing the retractor to the polyaxial bone screw, that can block the surgeon's view of the site. Such unwieldy parts severely inhibit a surgeons ability to visualize the construct at the surgical site and result in generally blind insertion and significant reliance on the instrumentation. Coupled with the metallic composition and bulky size of the instruments, visualization of the construct may not be possible until all of the instruments are removed from the construct and the incision at the conclusion of the procedure. Subsequently, if the finally implanted construct is not acceptable to the surgeon, the bulky and unwieldy instruments may have to be reattached to the construct or the surgeon may need to repair the construct through an open procedure.

The conventional minimally invasive spine instruments are typically bulky and unwieldy to react forces encountered by the relatively long, hollow sleeves or cannulae during final tightening of the locking caps to the pedicle screws. The hollow sleeves or cannulae are typically bulky and stiff specifically at the distal end portions to rigidly hold the arms of the pedicle screws in position during final tightening to prevent splaying of the pedicle screws under final tightening loads. In addition, the hollow sleeve or cannulae are bulky and unwieldy along their length to prevent twisting, splaying or breakage during the final tightening step. This metallic bulk attached to the construct limits visualization, as was described above.

BRIEF SUMMARY

It would be desirable to develop a minimally invasive spine instrument set that is relatively simple, utilizes relatively small components that improve fluoroscopic visualization of the screws and rod when the instruments are attached thereto and are relatively low-profile at the skin incision to permit maximum line-of-sight potential for the surgeon. It would also be desirable to construct a minimally invasive spine instrument set with a counter-torque tool that is relatively easy to secure to a screw for tightening of a locking cap and is relatively easy to remove and replace so that the instrument is only in the surgical theatre when necessary for tightening purposes. In addition, it is desirable to design and construct an instrument set that permits insertion of the locking cap into a minimally invasive incision utilizing a more robust retaining feature than the self-retaining tip of a screwdriver. Further, it is desirable to design and construct a set of minimally invasive instruments that enhances a surgeons line-of-sight during the procedure or while mounted to the construct and permits visualization utilizing fluoroscopy while the instruments are mounted to the construct. It is also desirable to construct a minimally invasive spine instrument set that maximizes visualization by reducing the bulk of the instruments without compromising strength during the final tightening step and preventing splaying of the instruments or the pedicle screws. It is further desirable to design and construct a system for minimally invasive spine surgery that allows for simple coupling and decoupling of a tissue retractor to and from the bone anchor or pedicle screw, eliminates excessive field-of-view blocking instrumentation, minimizes the incision, and limits splay and cross-threading while reducing excess tool replacement, thereby simplifying the surgical procedure.

Briefly stated, an exemplary instrument set for use in minimally invasive spine surgery includes a polyaxial bone screw and a tissue retractor having distal and proximal end portions and a partial pathway formed therebetween. The tissue retractor is removably couplable to the bone anchor and rotatably fixed to the bone anchor when coupled thereto. An instrument has distal and proximal end portions and a hollow cavity formed therebetween, and is removably couplable within the partial pathway of the tissue retractor and rotatably fixed to the tissue retractor when coupled thereto. A drive shaft has a diameter that is less than a diameter of the hollow cavity of the instrument and is rotatable with respect to the instrument when positioned therein. A counter-torque handle has a gripping end portion and an interlock end portion. The interlock end portion includes an instrument interface that is releasably positioned within the hollow cavity of the instrument at the proximal end portion thereof and is rotatably fixed thereto in an assembled configuration. The interlock end portion also includes an open-ended slot having a width that is greater than the diameter of the drive shaft such that the counter-torque handle is movable to and from the assembled configuration while the drive shaft is within the hollow cavity.

Another exemplary embodiment of the instrument set for performing minimally invasive spine surgery includes a polyaxial bone screw and a tissue retractor having a distal end portion configured to receive and removably couple to the polyaxial bone screw, a proximal end portion opposite the distal end portion, and a partial pathway formed at the distal end portion and extending toward the proximal end portion. The distal end portion of the tissue retractor includes a blocking rib projecting into the partial pathway of the tissue retractor and having an inner surface. An instrument has distal and proximal end portions and a hollow cavity formed therebetween. The instrument is received within the partial pathway of the tissue retractor in an assembled configuration such that the partial pathway of the tissue retractor and the hollow cavity of the instrument are coaxially aligned. The distal end portion of the instrument includes a blocking tab that is received by the blocking rib of the tissue retractor in the assembled configuration. The blocking tab contacts the inner surface of the blocking rib in the presence of a force exerted by the bone screw on an interior surface of the tissue retractor.

A further exemplary embodiment of an instrument set for performing minimally invasive spine surgery includes a polyaxial bone screw having a body and a bone screw. The body has a rod channel with a rod receiving portion disposed proximate the bone screw and a threaded portion distally located from the bone screw. A tissue retractor has a proximal end portion, a distal end portion, and a partial pathway extending longitudinally from the distal end portion toward the proximal end portion. The distal end portion is removably coupled to the body of the polyaxial bone screw. A locking cap has a threaded portion. A cap guide has a proximal end portion, a distal end portion, and a hollow cavity extending longitudinally therebetween. The locking cap is removably insertable into the hollow cavity of the cap guide and rotatable with respect to the cap guide when positioned therein. The cap guide is positioned within the partial pathway of the tissue retractor in the assembled configuration such that the partial pathway of the tissue retractor and the hollow cavity of the cap guide are coaxially aligned and the locking cap is coaxially aligned with the body of the polyaxial bone screw to permit mating of the threaded portion of the locking cap with the threaded portion of the body.

A still further exemplary embodiment of an instrument set for use in minimally invasive spine surgery includes a bone anchor having an outer surface with at least one recess. A tissue retractor is removably coupled to the bone anchor in an assembled configuration and includes a body having a proximal end portion and a distal end portion defining a longitudinal axis therebetween, a partial pathway extending longitudinally between the proximal and the distal end portions, a window accessing the partial pathway and formed in the body proximate the proximal end portion, and at least one cutout slot in the body extending generally longitudinally along a portion of the body proximate the distal end portion. The at least one cutout slot has proximal and distal end portions. A resiliently movable arm is defined by the at least one cutout slot, is movably attached to the body at the proximal end portion of the at least one cutout slot, and has an attachment tab projecting generally transverse to the longitudinal axis adjacent the distal end portion of the at least one cutout slot and a protrusion projecting generally transverse to the longitudinal axis adjacent the proximal end portion of the at least one cutout slot. The at least one tab is positioned within the at least one recess when the bone anchor and tissue retractor are in the assembled configuration. A removal tool has proximal and distal end portions and is received within the partial pathway of the tissue retractor in an engaged position. The removal tool includes a body having a proximal end portion and a distal end portion and at least one protrusion extending from the removal tool body proximate the distal end portion. The at least one protrusion is configured to engage the corresponding protrusion of the resiliently movable arm of the tissue retractor in the engaged position to cause the tab of the resiliently movable arm to be spaced apart from the recess of the bone anchor. A resilient tab is disposed proximate the proximal end portion of the removal tool body. The resilient tab has (1) a relaxed position wherein when the tissue retractor and removal tool are in the engaged position, the resilient tab projects from the body of the removal tool and is positioned within the window of the tissue retractor, rotatably fixing the tissue retractor and the removal tool to permit removal of the tissue retractor from the bone anchor, and (2) a depressed position wherein the resilient tab is depressed toward the body of the removal tool to permit insertion or removal of the removal tool from the partial pathway of the tissue retractor.

BRIEF DESCRIPTION OF THE SEVERAL VIEWS OF THE DRAWINGS

The foregoing summary, as well as the following detailed description of the device and method, will be better understood when read in conjunction with the appended drawings. For the purpose of illustrating the device and method of the present application, there is shown in the drawings exemplary embodiments. It should be understood, however, that the exemplary device and method are not limited to the precise arrangements and instrumentalities shown. In the drawings:

FIG. 7 is a top perspective view of a counter-torque handle in accordance with the exemplary embodiment the instrument set;

FIG. 16 is a side elevational view of one component of a two-piece tissue retractor for use with the exemplary embodiment of the instrument set;

FIG. 17 is a side perspective view of the two-piece tissue retractor of FIG. 16 coupled to the pedicle screw of FIG. 1;

DETAILED DESCRIPTION

Figure 1:
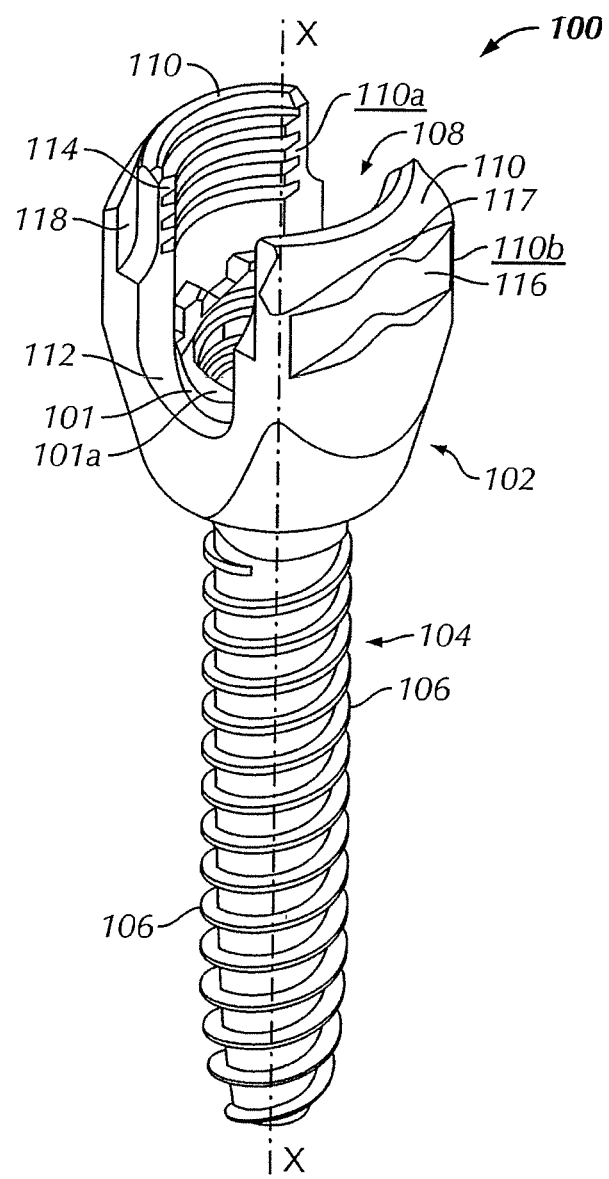
FIG. 1 is a top perspective view of a first exemplary embodiment of a bone anchor assembly or polyaxial pedicle screw without a locking cap (See FIG. 11) for use with an exemplary embodiment of a minimally invasive instrument set.

Certain terminology is used in the following description for convenience only and is not limiting. The words "right,"

"left," "lower," and "upper" designate directions in the drawings to which reference is made. The words "inwardly" or "distally" and "outwardly" or "proximally" refer to directions toward and away from, respectively, the geometric center or orientation of the exemplary instrument set and related parts thereof. The words, "anterior," "posterior," "superior," "inferior," "lateral," "medial," and related words and/or phrases designate exemplary positions and orientations in the human body to which reference is made and are not meant to be limiting. The terminology includes the above-listed words, derivatives thereof and words of similar import.

Figure 2:
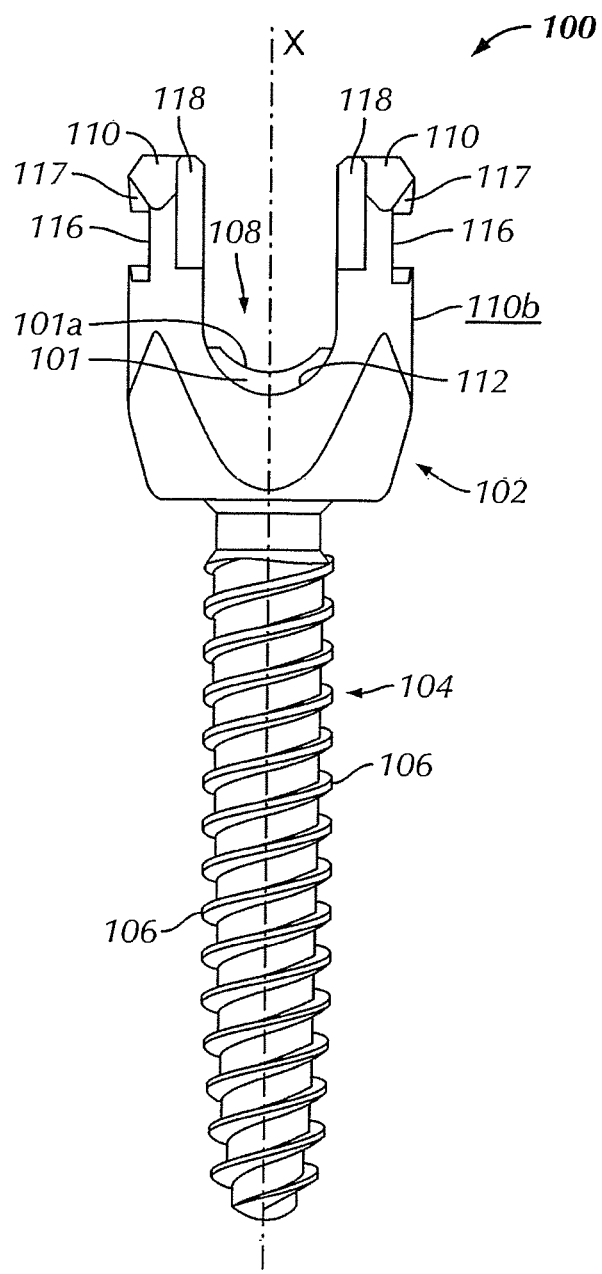
FIG. 2 is a front elevational view of the bone anchor assembly or polyaxial pedicle screw of FIG. 1.
Figure 3:
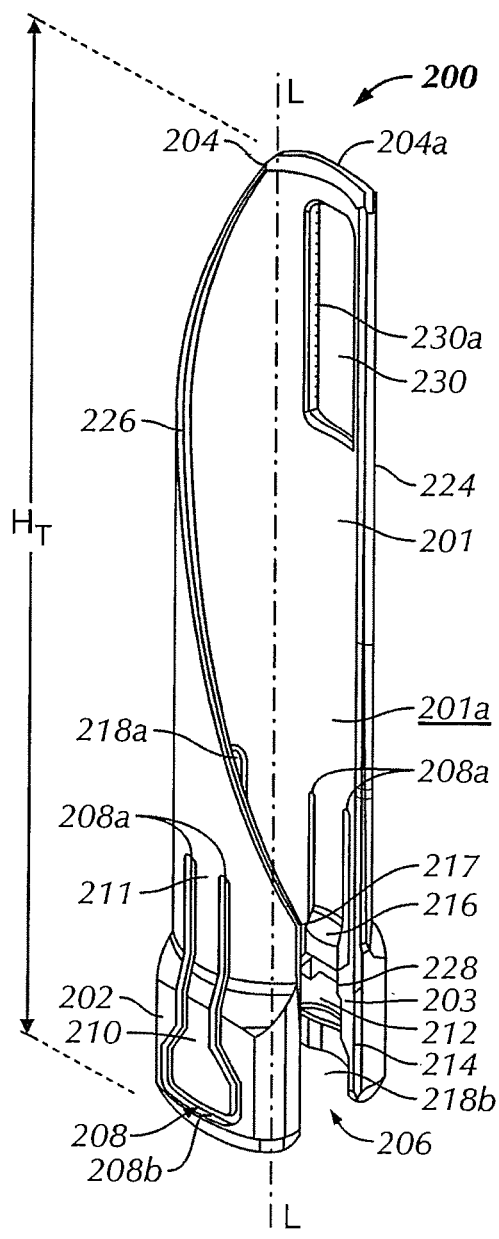
FIG. 3 is a side perspective view of a tissue retractor in accordance with the exemplary embodiment of the instrument set.
Figure 4:
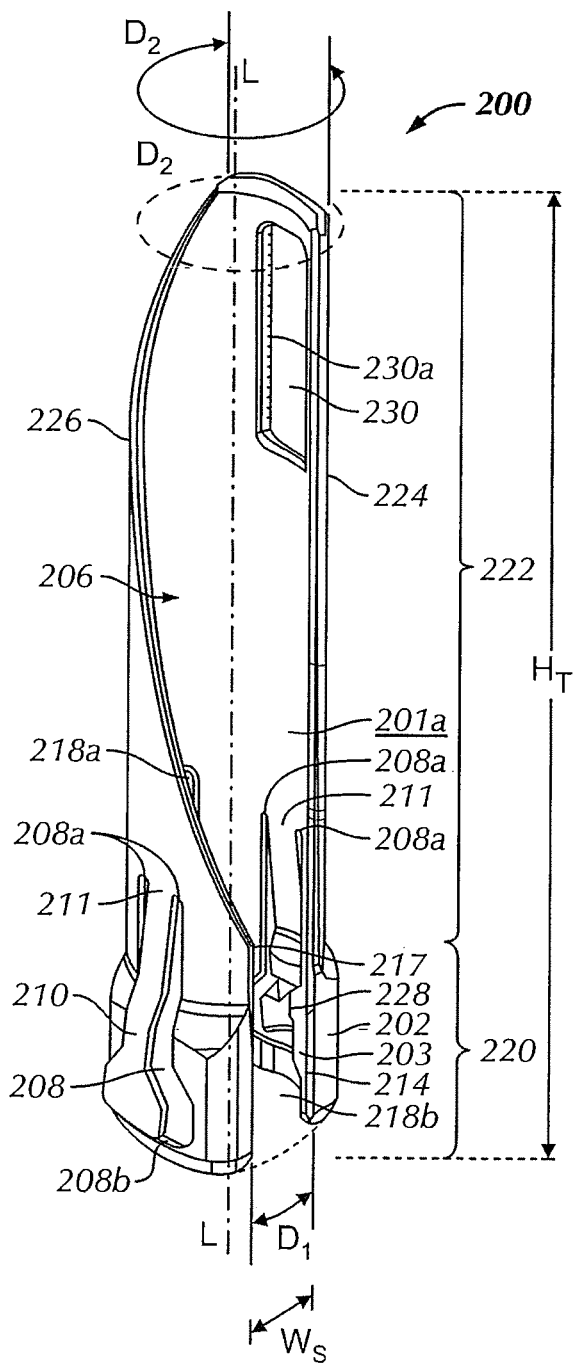
FIG. 4 is a side perspective view of the tissue retractor of FIG. 3 with resiliently movable arms thereof in a flexed position.
Figure 11:
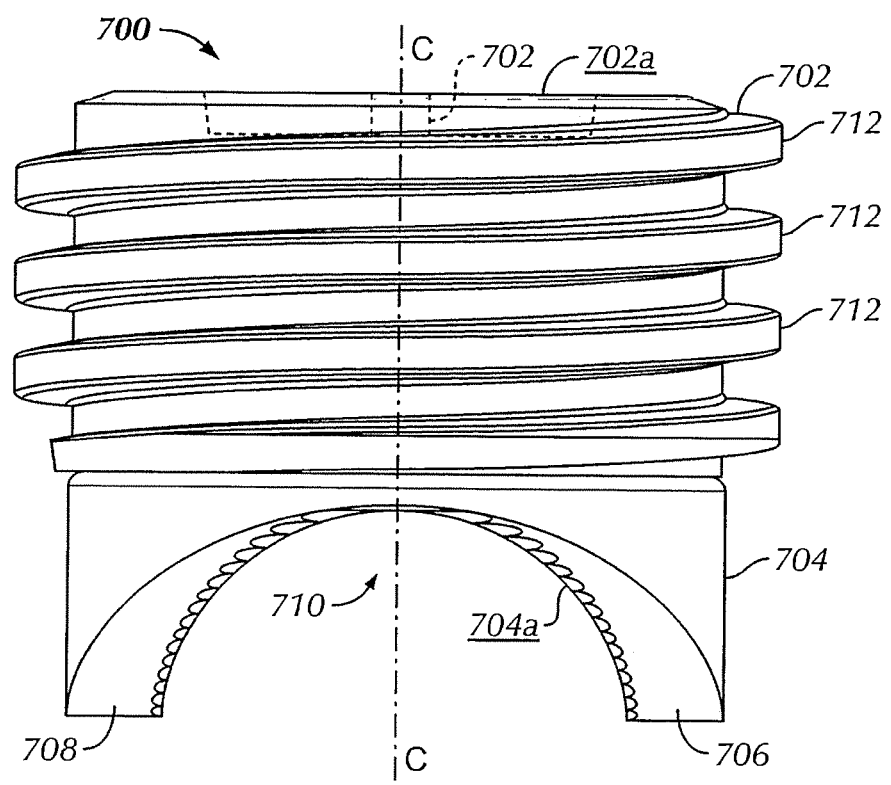
FIG. 11 is a greatly enlarged front elevational view of the exemplary locking cap of the pedicle screw of FIG. 1 in accordance with the exemplary embodiment.

FIGS. 1, 2 and 11 show an exemplary bone anchor assembly, polyaxial bone screw or polyaxial pedicle screw 100 for use with an exemplary instrument set for minimally invasive spine surgery includes a body 102, a locking cap or a bone screw cap 700 and a threaded portion or bone screw 104. Although the figures and description of the present application show and describe the exemplary polyaxial bone screw 100, it will be apparent to one having ordinary skill in the art based upon a review of the present disclosure that the exemplary instrument set may be modified and adapted to function with a monoaxial bone screw (not shown). The exemplary instrument set may also be adapted to operate and function with numerous styles of pedicle screws and is not limited to functioning with the exemplary pedicle screw 100.

The bone screw 104 includes a plurality of threads 106 for securing the polyaxial pedicle screw 100 to a vertebra V (FIG. 14) of a patient. The body 102 is polyaxially mounted to the bone screw 104 such that the bone screw 104 is rotatable and pivotable with respect to the body 102. A locking collar or collet 101 is mounted within the body 102 and is positioned between the body 102 and a head of the bone screw 104 in an assembled configuration. The locking collar 101 facilitates the polyaxial movement of the bone screw 104 relative to the body 102 and locking of the body 102 relative to the bone screw 104 in a locked configuration. An example of a polyaxial bone screw 100 that may be utilized with the exemplary minimally invasive instrument set is described in International Patent Application Publication No. WO 2009/015100 ("WO 100"), titled, "Polyaxial Bone Fixation Element" and filed, Jul. 21, 2009, which is incorporated herein by reference in its entirety.

The polyaxial bone screw 100 is generally constructed of titanium or a titanium alloy, such as an alloy including Titanium, Aluminum and Niobium (TAN—TI-6Al-6Nb—ASTM F 1295) but may also be constructed of stainless steel, other metallic alloy materials or nearly any strong, stiff, biocompatible material that is able to take on the general size and shape of the polyaxial bone screw 100 and withstand the normal operating conditions of the polyaxial bone screw 100. The polyaxial bone screw 100, particularly the bone screw 104, may be provided having different lengths and/or diameters to accommodate anatomical variations and bone structure of specific patients. The bone screw 104 may be cannulated (not shown) along a central longitudinal screw axis X-X thereof for positioning and placement of the polyaxial bone screw 100 over a Kirschner wire or guide wire (K wires) (not shown) for guidance of the bone screw 104 to the site of implantation on the vertebra V.

The body 102 includes a generally U-shaped rod slot or channel 108 defined by two arms 110. The collet 101 includes a rod saddle 101a that is aligned with the rod channel 108 in an assembled configuration and receives and contacts a spinal rod R (FIG. 10C) in a locked configuration. The rod channel 108 terminates proximate the collet 101 in an assembled configuration to form a rod receiving portion 112 that is sized to accommodate the rod R (FIG. 10C). Each arm 110 includes an interior surface 110a having a threaded portion 114 located distally from the bone screw 104 in the assembled configuration. An outer surface 110b of each arm 110 typically includes a recess 116 therein.

Referring to FIGS. 1-5, 9 and 10A-10C, a tissue retractor 200 of the exemplary instrument set for minimally invasive spine surgery for use with the bone anchor assembly 100 includes a body 201 with a distal end portion 202, a proximal end portion 204 and a longitudinal tissue retractor axis L-L extending between the distal and proximal end portions 202, 204. The body 201 includes first and second slots 218a, 218b at the distal end portion 202 and first and second longitudinally extending edges 224, 226 that define the second slot 218b at the distal end portion 202. The longitudinally extending edges 224, 226 extend between the distal and proximal end portions 202, 204. The first longitudinally extending edge 224 is generally parallel with the longitudinal tissue retractor axis L-L of the tissue retractor 200, but is not so limited and may extend in nearly any path or include changes in direction along its length to adapt the design of the tissue retractor 200 to particular applications. The second longitudinally extending edge 226 is generally parallel with the longitudinal tissue retractor axis L-L at the distal end portion 202 and curves in a helix-like shape from an inflection point 217 near the distal end portion 202 toward the proximal end portion 204 such that the tissue retractor 200 has less structure than an enclosed or substantially enclosed cannula or sleeve. In this manner, the tissue retractor 200 may provide a more forgiving line-of-sight to a surgeon at a skin incision I and to limit material of the tissue retractor 200, particularly adjacent the skin incision I. Limiting the amount of instrument grade stainless steel or other difficult to image material of the tissue retractor 200 may not only provides improved line-of-sight for the surgeon, but may also reduce the amount of interference with imaging systems, such as fluoroscopy, when a surgeon images the spinal construct with the tissue retractor 200 mounted to the polyaxial bone screw 100. Further, reducing the amount of material of the tissue retractor 200 that extends out of the skin incision I generally reduces the size of the skin incision I.

The body 201 is typically constructed of instrument grade stainless steel but may also be constructed of titanium, aluminum, metallic alloys, polymeric materials, composite materials or nearly any relatively stiff, strong, biocompatible material that is able to take on the general shape of the tissue retractor 200 and withstand the normal operating conditions of the tissue retractor 200. A partial pathway 206 extends longitudinally between the distal and proximal end portions 202, 204 and is defined by the first and second longitudinally extending edges 224, 226 and an inner surface 201a of the body 201. The partial pathway 206 is nearly completely exposed along a majority of the length of the tissue retractor 200 as a result of the helix-shape of the second longitudinally extending edge 226 such that the tissue retractor 200 functions to retract tissue, as will be described in greater detail below.

The body 201 generally defines a perimeter about the longitudinal tissue retractor axis L-L. The body 201 includes a first portion 220 adjacent the distal end portion 202 and a second portion 222 extending longitudinally from the proximal end portion 204 to the inflection point 217. A terminal portion 204a of the proximal end portion 204 has a generally linear and slightly curved cross-section. The body 201 also includes at least one, but typically two, cutout slots 208 extending generally longitudinally along a portion of the body 201 proximate the distal end portion 202. The two cutout slots 208 are disposed opposite one another proximate the distal end portion 202. Each cutout slot 208 includes a pair of proximal end portions 208a and a distal end portion 208b. A resiliently movable arm 210 is defined by each cutout slot 208. The arm 210 is movably attached to the body 201 at the proximal end portions 208a of the cutout slot 208, by a deflection area 211, although other configurations for attaching the arm 210 to the body 201 may be utilized, such as a spring-biased hinge or alternate mechanisms that permit the arm 210 to pivot or flex relative to the body 201. The body 201 also includes a window 230 near the proximal end portion 204 that may be utilized to engage or removably couple the tissue retractor 200 to various tool and/or instruments, as will be described in greater detail below.

Figure 5:
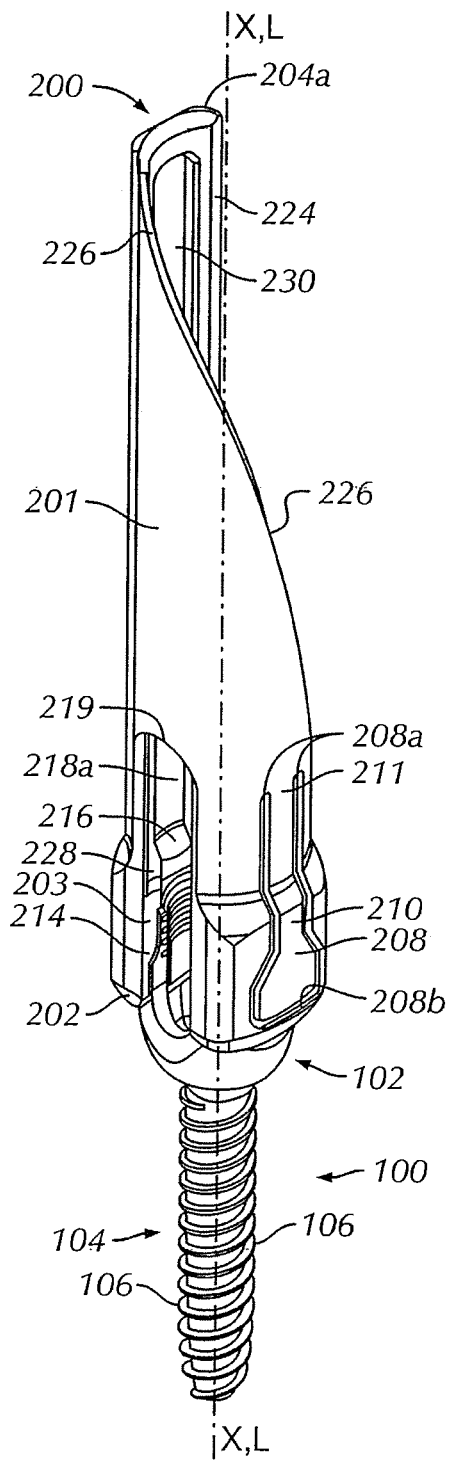
FIG. 5 is a side perspective view of the pedicle screw of FIG. 1 coupled to the tissue retractor of FIG. 3.
Figure 6A:
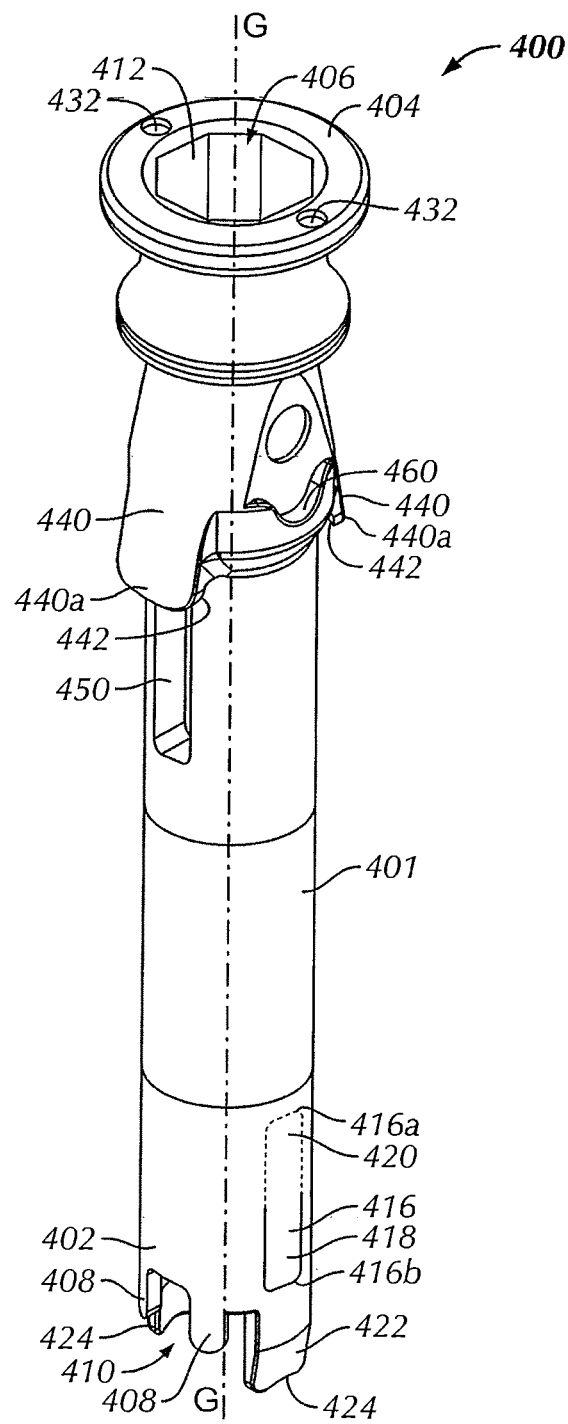
FIG. 6A is a right-side perspective view of a cap guide instrument in accordance with the exemplary embodiment of the instrument set.
Figure 6B:
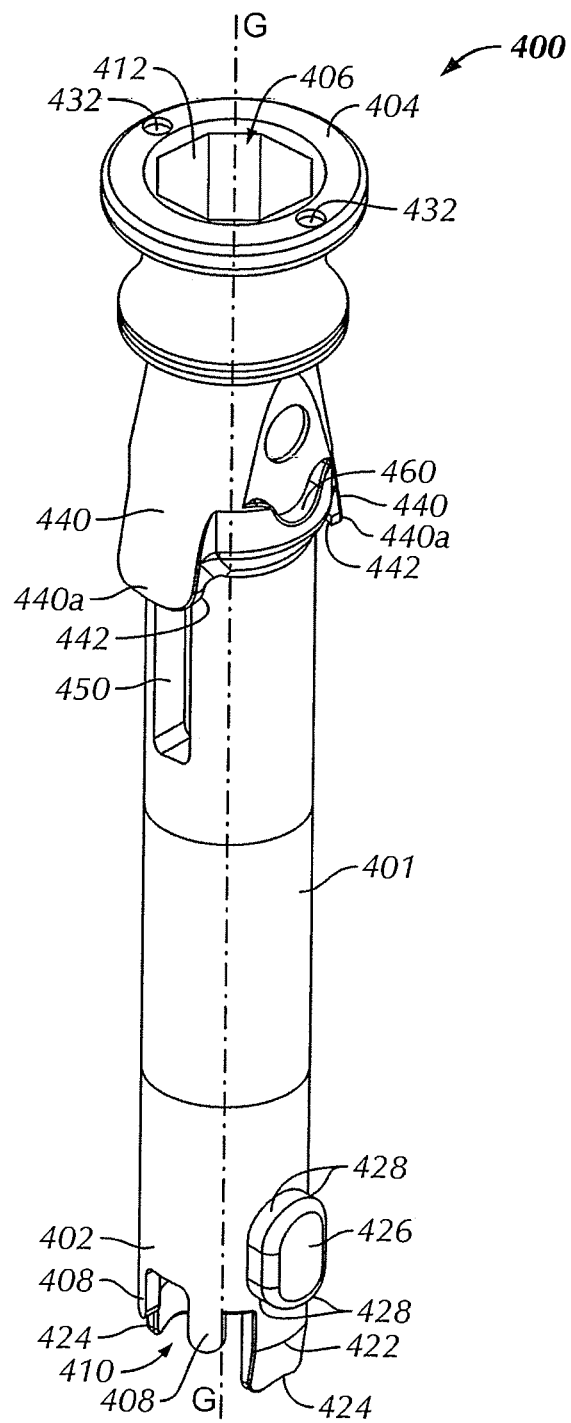
FIG. 6B is a left-side perspective view of the cap guide instrument of FIG. 6A.

The tissue retractor 200 is removably couplable to the polyaxial bone screw 100 and is rotatably fixed to the polyaxial bone screw 100 when coupled thereto in an assembled configuration (FIG. 5). A portion of the inner surface 201a of the body 201 receives and contacts a portion of the outer surfaces 110b of the arms 110 of the body 102 in the assembled configuration, thereby restricting movement of the body 102 of the polyaxial bone screw 100 relative to the tissue retractor 200 in a plane perpendicular to the longitudinal axis L. The tissue retractor 200 also includes at least one and typically four screw engagement ribs 214 (FIGS. 3-5 and 8) extending longitudinally and inwardly toward the longitudinal tissue retractor axis L-L from the distal end portion 202, generally toward the partial pathway 206. The body 102 of the polyaxial bone screw 100 includes a corresponding number of complementary collar grooves 118 (FIGS. 1 and 2) extending longitudinally from a proximal end portion 102a of the body 102. Each screw engagement rib 214 mates with one of the corresponding collar grooves 118 when the tissue retractor 200 is coupled to the polyaxial bone screw 100 such that the distal end portion 202 surrounds and grasps the arms 110, thereby restricting rotation of at least the body 102 about the longitudinal axis L. However, when the tissue retractor 200 is mounted to the body 102, the tissue retractor 200 and body 102 are pivotable and rotatable relative to the bone screw 104, at least until the body 102 is locked relative to the bone screw 104, as will be described in greater detail below. Engagement of the screw engagement ribs 214 with the collar grooves 118 provide a relatively bulky thickness, particularly at bulked-up portions 203, relative to the remainder of the body 201 such that the distal end portion 202 of the tissue retractor 200 and, particularly, the screw engagement ribs 214 are able to react final tightening forces resulting from final tightening of the locking cap 700 to the body 102, as will be described in greater detail below.

The arm 210 of the tissue retractor 200 includes an attachment tab 212 located adjacent to the distal end portion 208b of the respective cutout slot 208, which projects generally transverse to and inwardly toward the longitudinal tissue retractor axis L-L. The arm 210 has a relaxed position (FIGS. 3 and 5), wherein, when the bone anchor assembly 100 and the tissue retractor 200 are in the assembled configuration, the attachment tab 212 is positioned within the recess 116 of the body 102 of the bone anchor assembly 100 (FIG. 5). Longitudinal movement of the body 102 within the partial pathway 206 along the longitudinal tissue retractor axis L is thereby restricted when the tissue retractor 200 is mounted to the body 102. The arm 210 also has a flexed position (FIG. 4), wherein the arm 210 is deflected outwardly from the tissue retractor 200, thus spacing the attachment tab 212 from the recess 116 of the bone anchor assembly 100 to permit longitudinal removal of the tissue retractor 200 from the body 102 or to permit the attachment tab 212 to move into the recess 116 without interfering or being blocked by a locking edge 117 of the body 102.

When the tissue retractor 200 is engaged to the body 102 with the screw engagement ribs 214 positioned within the collar grooves 118, five degrees of freedom of movement of the tissue retractor 200 are limited relative to the body 102 by the engagement of the engagement ribs 214 with the collar grooves 118. Specifically, the tissue retractor 200 is generally limited in any rotational movement and any translational movement except for movement away from the body 102 along the longitudinal tissue retractor axis L-L by engagement of the engagement ribs 214 with the collar grooves 118. The engagement of the attachment tab 212 with the recess 116 and/or locking edge 117 generally blocks movement of the tissue retractor 200 along the longitudinal tissue retractor axis L-L away from the body 102 and the final potential degree of freedom of movement of the tissue retractor 200 relative to the body 102. The attachment tab 212 may be sized and configured such that no clamping force is applied by the attachment tab 212 to the sides of the body 102 when the attachment tab 212 is positioned within the recess 116, as the attachment tab 212 may be configured to block axial movement of the tissue retractor 200 away from the body 102 in the engaged position, as opposed to any additional degrees of freedom. Accordingly, the attachment tab 212 may only block movement of the tissue retractor 200 away from the body through interference between the attachment tab 212 and the locking edge 117 of the recess 116.

The tissue retractor 200 also generally includes at least one retaining tab 216 proximate the distal end portion 202 of the body 201 that projects from the inner surface 201a into the partial pathway 206. The retaining tab 216 is typically positioned on the inner surface of the movable arm 210 proximally or above the attachment tab 212. However, the retaining tab 216 may be located elsewhere within the partial pathway 206. When the bone anchor assembly 100 is coupled to the tissue retractor 200, the proximal end portion 102a of the body 102 abuts the retaining tab 216 (FIG. 5), thereby preventing further movement of the bone anchor assembly 100 along the longitudinal axis L into the partial pathway 206.

The tissue retractor 200 also includes at least one, typically the first and second slots 218a, 218b, formed at the distal end portion 202 that extend longitudinally from the distal end portion 202 toward the proximal end portion 204. The first slot 218a of the exemplary embodiment does not extend the entire length of the tissue retractor 200 and terminates at a closed end portion 219. When the polyaxial bone screw 100 is coupled to the tissue retractor 200, the first and second slots 218a, 218b are aligned with the rod channel 108 of the body 102. The second slot 218b is defined in the first portion 220 of the body 201 by the first and second longitudinally extending edges 224, 226 of the body 201 that are separated by a first predetermined distance $D_1$ about the perimeter. In the second portion 222 of the body 201 between the inflection point 217 and the proximal end portion 204, a distance about an imaginary perimeter between the first and second edges 224, 226 increases along the longitudinal tissue retractor axis L-L from the first predetermined distance $D_1$ to a second predetermined distance $D_2$ at the proximal end portion 204 of the body 201. The first edge 224 is generally linear and remains at a relatively fixed position on the perimeter along the length of the second portion 222 while the second edge 226 progressively moves farther away in a curvilinear or helix-like manner along the length of the second portion 222 to create the greater distance D2 at or near the proximal end portion 204. For example, the tissue retractor 200 shown in FIGS. 3 and 4 exhibits the helical-like cut to the second edge 226, although other cuts, such as a linear slant, taper, curve, or the like may be used. Further, both the first and second edges 224, 226 may exhibit the helix-like shape without significantly impacting the function of the tissue retractor 200 of the exemplary instrument set.

Figure 10A:
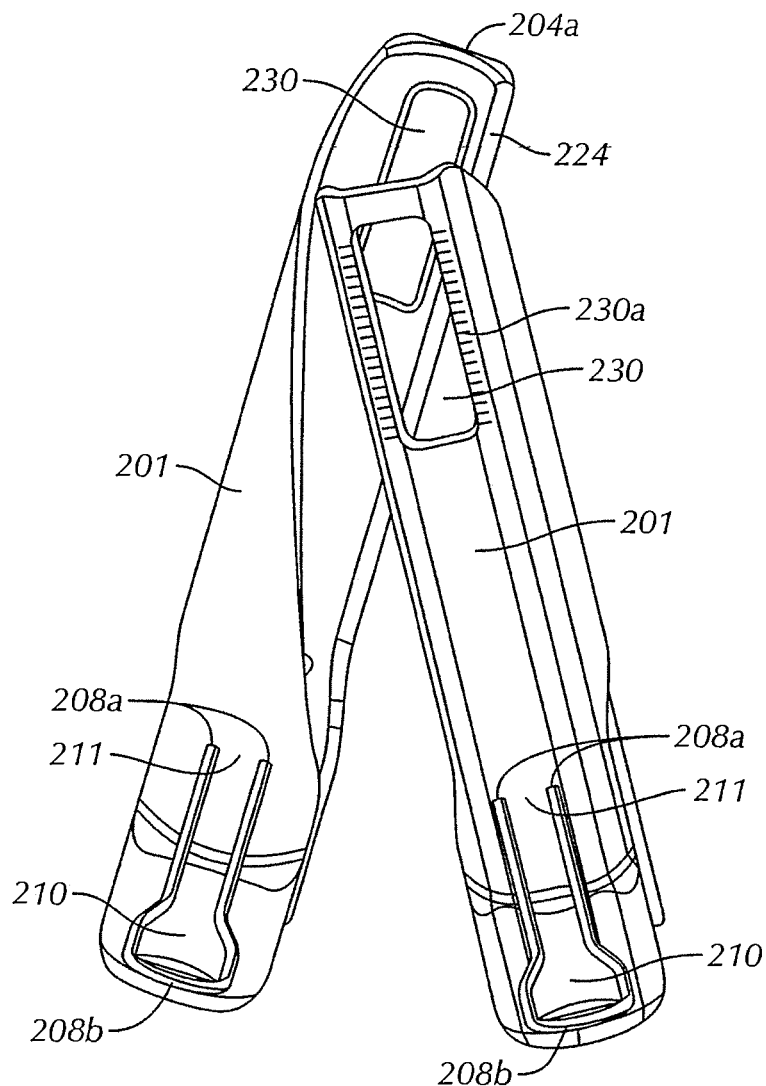
FIG. 10A is a side perspective view of two tissue retractors of FIG. 3 in a partially nested configuration.
Figure 10B:
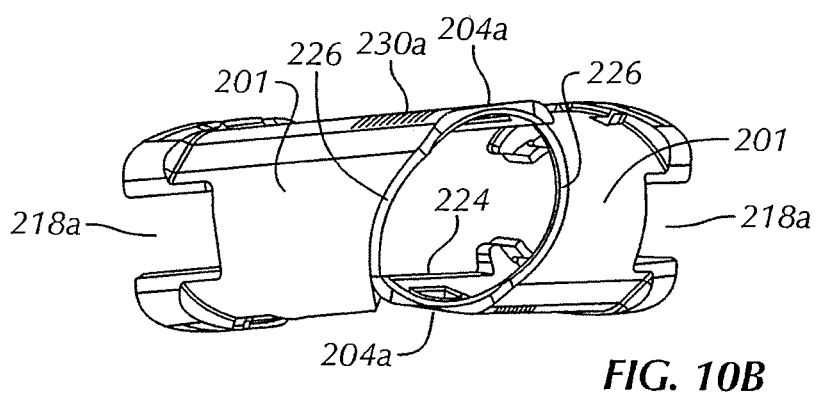
FIG. 10B is a top perspective view of the two tissue retractors of FIG. 11A.
Figure 10C:
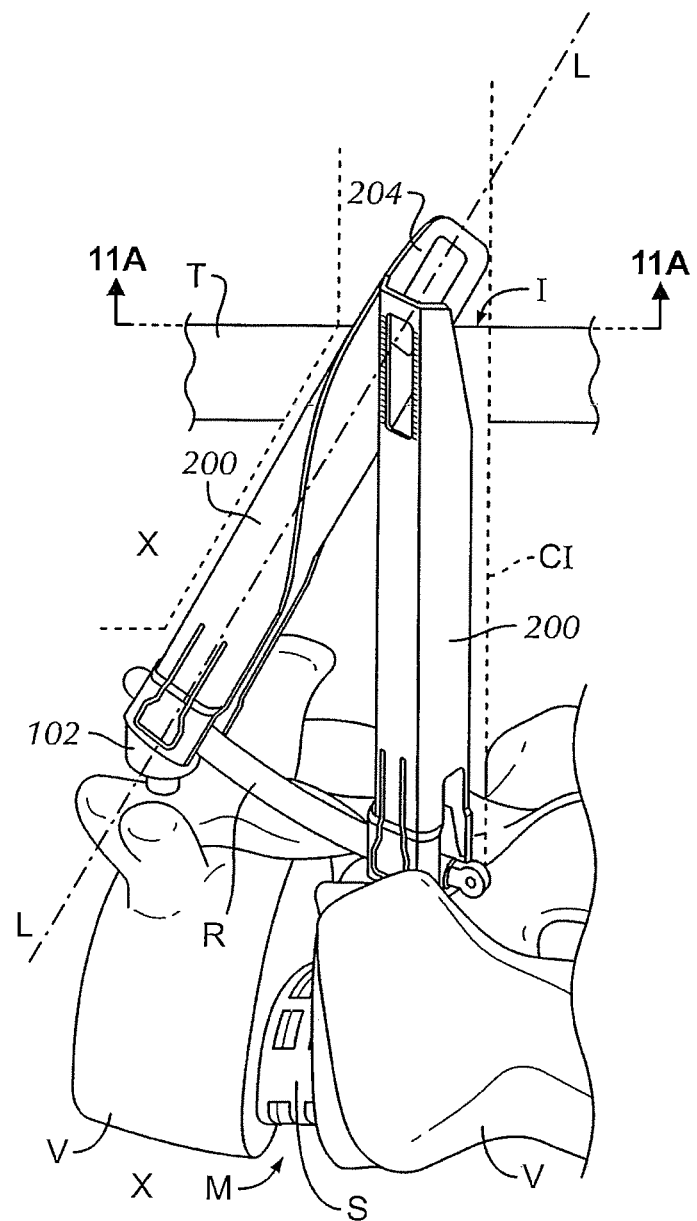
FIG. 10C is a side perspective view of the two tissue retractors of FIG. 3 and two bone anchors of FIG. 1 secured to adjacent vertebrae in a surgical procedure.

Referring to FIGS. 3-5 and 10A-10C, as shown in use, the tissue retractor 200 may reduce the invasiveness of a surgical procedure performed at a motion segment M including a superior and inferior vertebrae V of a patient's spine. For example, in the exemplary embodiment, two tissue retractors 200 having the partial pathways 206 and the helix-like second edge 226 are mounted to polyaxial bone screws 100 and are angled toward one another into a nested or partially nested configuration (FIGS. 10A-10C), which may reduce the size of the skin incision I. Specifically, the relatively open proximal end portions 204 of the tissue retractors 200 are able to nest at the skin incision I such that a relatively small skin incision I is required. Conventional, enclosed minimally invasive sleeves or cannulae require an incision that accommodates at least twice the diameter of a single sleeve or cannula as the cross-section of these conventional, enclosed minimally invasive sleeves or cannulae form at least a figure eight (8) at the skin incision level. In contrast, the skin incision I required to accommodate the nested tissue retractors 200 may be less than a full diameter of one of the tissue retractors 200, because in the nested configuration the tissue retractors 200 have an mirrored, arcuate-shape or eye-shape (FIG. 10B). In addition, a patient's soft tissue T tends to bias the tissue retractors 200 toward the nested configuration. Further, the tissue retractors 200 may be separated from the nested configuration by the surgeon or utilized in a similar manner to a retractor to spread the skin incision I or move the soft tissue T to change the position of the skin incision I to maximize the surgeon's line-of-site to specific areas of the surgical site or elements of the construct, as long as the bodies 102 remain polyaxially rotatable relative to the bone screws 140.

The tissue retractors 200 typically have a height HT that is slightly greater than a distance from the implanted polyaxial bone screw 100 at the vertebra V to the skin incision I. Accordingly, the tissue retractor 200 extends only slightly outside of the skin incision I which may provide an increased line-of-sight into a generally conical incision CI for viewing the surgical site and the impacted motion segment M. The tissue retractor 200 is also relatively simple to attach to the polyaxial bone screw 100 utilizing a snap-on action, as was described above, and is a single piece of structure that attaches to the body 102 for use by the surgeon in a similar manner to a retractor blade.

The generally conical incision CI can be made through the patient's soft tissue T to provide access to the motion segment M. The generally conical incision CI is made possible by the nesting of the tissue retractors 200 at their proximal end portions 204 as a result of the helix-like second edges 226. The resulting nesting permits a relatively oblong or eye-shaped single skin incision I (FIGS. 10B and 10C). Further, the tissue retractors 200 are generally sized to extend only a slight amount from the skin incision I to further limit structure and relative clutter in the line-of-sight of the surgeon.

Two bone anchor assemblies 100 can be guided through the generally conical incision CI via a K-wire (not shown) to the superior and inferior vertebrae V, respectively, and are screwed into the vertebrae V. The surgeon may create the conical incision CI by blunt dissection using their finger guided by the Longissimus and Multifidus muscles, which may lead the surgeon to the pedicles of the superior and inferior vertebrae V. Referring specifically to FIGS. 10A-10C, the tissue retractors 200 may also be inserted through the generally conical incision CI at the same time that the bone anchor assemblies 100 are inserted into the generally conical incision CI or may be subsequently coupled to the bone anchor assemblies 100 after mounting the bone anchor assemblies 100 to the vertebrae V. The bone anchor assemblies 100 may be inserted through the conical incision CI with our without the tissue retractors 200 mounted thereto, but the tissue retractors 200 are typically mounted to the bone anchor assemblies 100 during insertion into the generally conical incision CI. The rod R is inserted through the generally conical incision CI as the tissue retractors 200 retract or hold the patient's soft tissue T away from the rod R. The utilization of the tissue retractors 200 mounted to the polyaxial bone screws 100 permits the surgeon to pivot and rotate the proximal end portions 204 of the tissue retractors 200 into several different orientations and locations to maximize the line-of-sight to the surgical site, as the soft tissue T is somewhat elastic and pliable such that the skin incision I and conical incision CI may be manipulated or otherwise moved by the surgeon. Such manipulation of the incisions I, CI is typically not possible with conventional minimally invasive spine instrumentation wherein tubes, sleeves or cannulae are fixed together in a predetermined arrangement, because the tubes, sleeves or cannulae extending from the polyaxial bone screws are locked together, thereby preventing manipulation of the location, size and/or orientation of the incision or incisions.

The incision utilized for the tissue retractors 200 of a one-level surgery utilizing the exemplary instrument set is typically referred to as a mini-open incision. The exemplary mini-open incision results in the surgeon working through a single, generally conical incision CI with at least two polyaxial bone screws 100 and the spinal rod R included in the construct. The skin incision I of the generally conical incision CI may be utilized to mount one, two or additional level constructs into both lateral pedicles through a single mini-open midline incision by manipulating the incision I, CI over muscle planes on either side of the midline and dissecting to the motion segment M along muscle planes of the soft tissue T.

Referring to FIGS. 16 and 17, when a surgery is performed across at least two motion segments M, first and second tissue retractors 300a, 300b may be mounted to a central bone screw 100. In an assembled configuration, the first and second tissue retractors 300a, 300b define a two-piece tissue retractor 300 that may be used with the central or otherwise interiorly positioned bone screw 100. The first and second tissue retractors 300a, 300b are similar to the one-piece retractor 200 described above. Like numerals have been used for like elements, except the 300 series numerals have been used for the first and second tissue retractors 300a, 300b. Accordingly, a complete description of the individual tissue retractors 300a, 300b has been omitted, with only the differences being described. In the exemplary embodiment, the two-piece tissue retractor 300 includes the first tissue retractor 300a and the second tissue retractor 300b, each of which is removably couplable to a respective one of the arms 110 of the body 102 of the polyaxial bone screw 100. Each of the first and second tissue retractors 300*a*, 300*b* includes a body 301 with a distal end portion 302 and a proximal end portion 304 defining the longitudinal axis L-L and a partial pathway 306 defined between the proximal and distal end portions 302, 304. When coupled to the polyaxial bone screw 100, the first and second tissue retractors 300*a*, 300*b* hold back soft tissue T creating a void 307 that permits insertion of the rod R into the patient. The first and second tissue retractors 300*a*, 300*b* may be utilized individually with the bone screw 100, but utilizing the pair of the first and second tissue retractors 300*a*, 300*b* with the bone screw 100 is utilized to define the void from the incision I to the bone screw 100 to accommodate introduction of the rod R into the bone screw 100.

The first and second tissue retractors 300*a*, 300*b* each include an inner surface 301*a*, a portion of which receives and typically contacts a portion of the outer surface 100*b* of a respective one of the arms 110, similar to the connection described above with respect to the one-piece tissue retractor 200. The inner surface 301*a* may have a curvature to define the partial pathway 306. Similarly, each of the first and second tissue retractors 300*a*, 300*b* includes a resiliently movable arm 310 defined by a cutout slot 308 of the body 301, screw engagement ribs, and a retaining tab 316, which function similarly to corresponding portions of the one-piece tissue retractor 200, and will not be described in further detail. When coupled to the polyaxial bone screw 100, the first and second tissue retractors 300*a*, 300*b* form at least one rod channel 318 extending longitudinally from the distal end portions 302 to the proximal end portions 304. The rod receiving channel 318 of the assembled first and second tissue retractors 300*a*, 300*b* is aligned with the rod channel 108 in the assembled configuration.

Referring to FIGS. 3-6B, 8 and 9, an exemplary cap guide instrument 400 includes a generally cylindrical sleeve 401 having a distal end portion 402, a proximal end portion 404 and a generally cylindrical, hollow cavity 406 extending between the distal and proximal end portions 402, 404 along a longitudinal guide axis G-G. The cap guide 400 is generally constructed of instrument grade stainless steel but may also be constructed of titanium, aluminum, metallic alloys, polymeric materials, composite materials or nearly any relatively stiff, strong, biocompatible material that is able to take on the general shape of the cap guide 400 and withstand the normal operating conditions of the cap guide 400. The cap guide 400 and any of the additional components of the exemplary instrument set may particularly be constructed of Aluminum, an Aluminum alloy or a polymeric material, particularly if improved imaging compatibility is desired.

Figure 8:
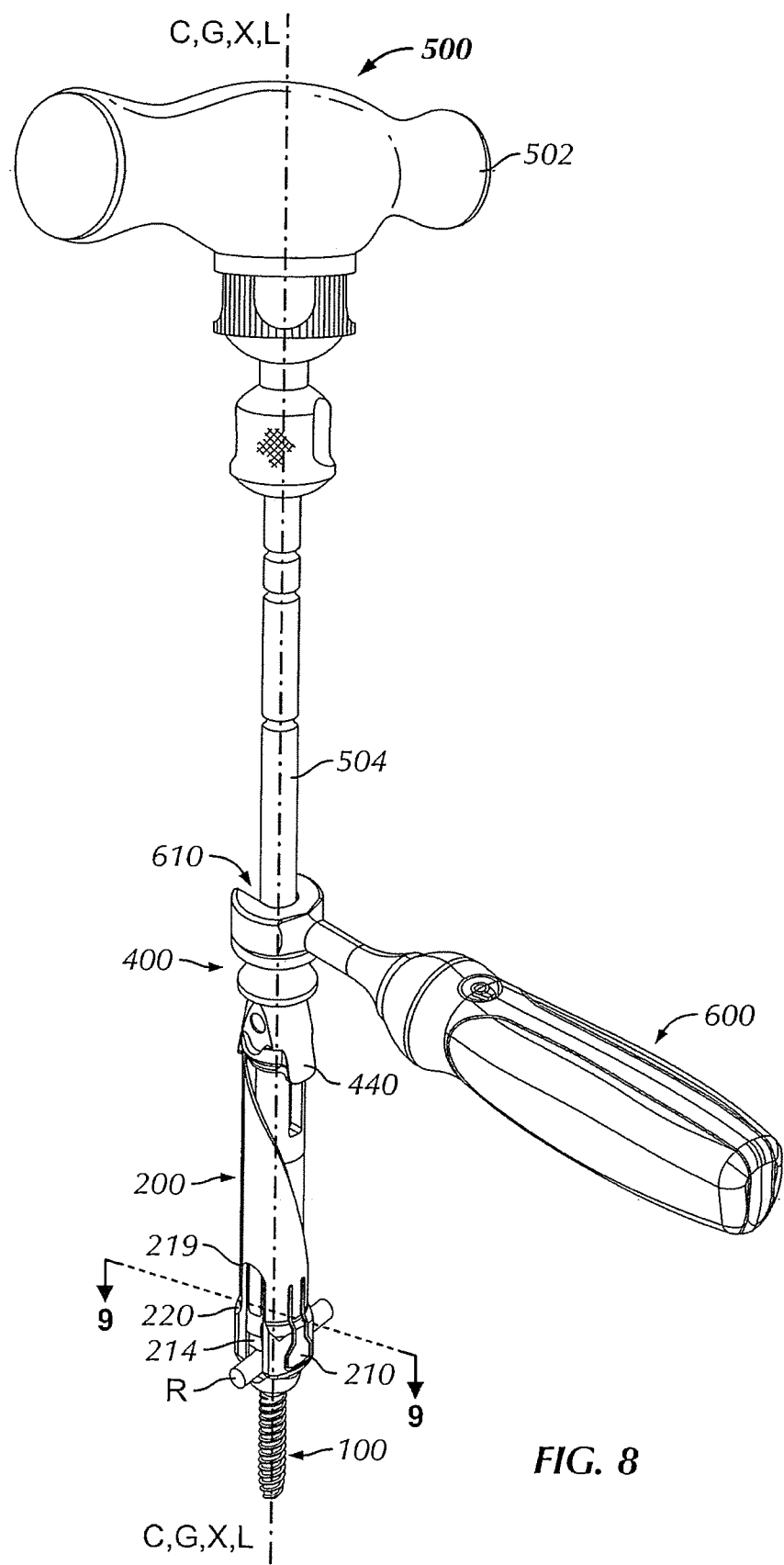
FIG. 8 is a side perspective view of the pedicle screw of FIG. 1, the tissue retractor of FIG. 3, the cap guide instrument of FIG. 6A, the counter-torque handle of FIG. 7, and a screwdriver in an assembled or working configuration in accordance with the exemplary embodiment the instrument set.
Figure 19A:
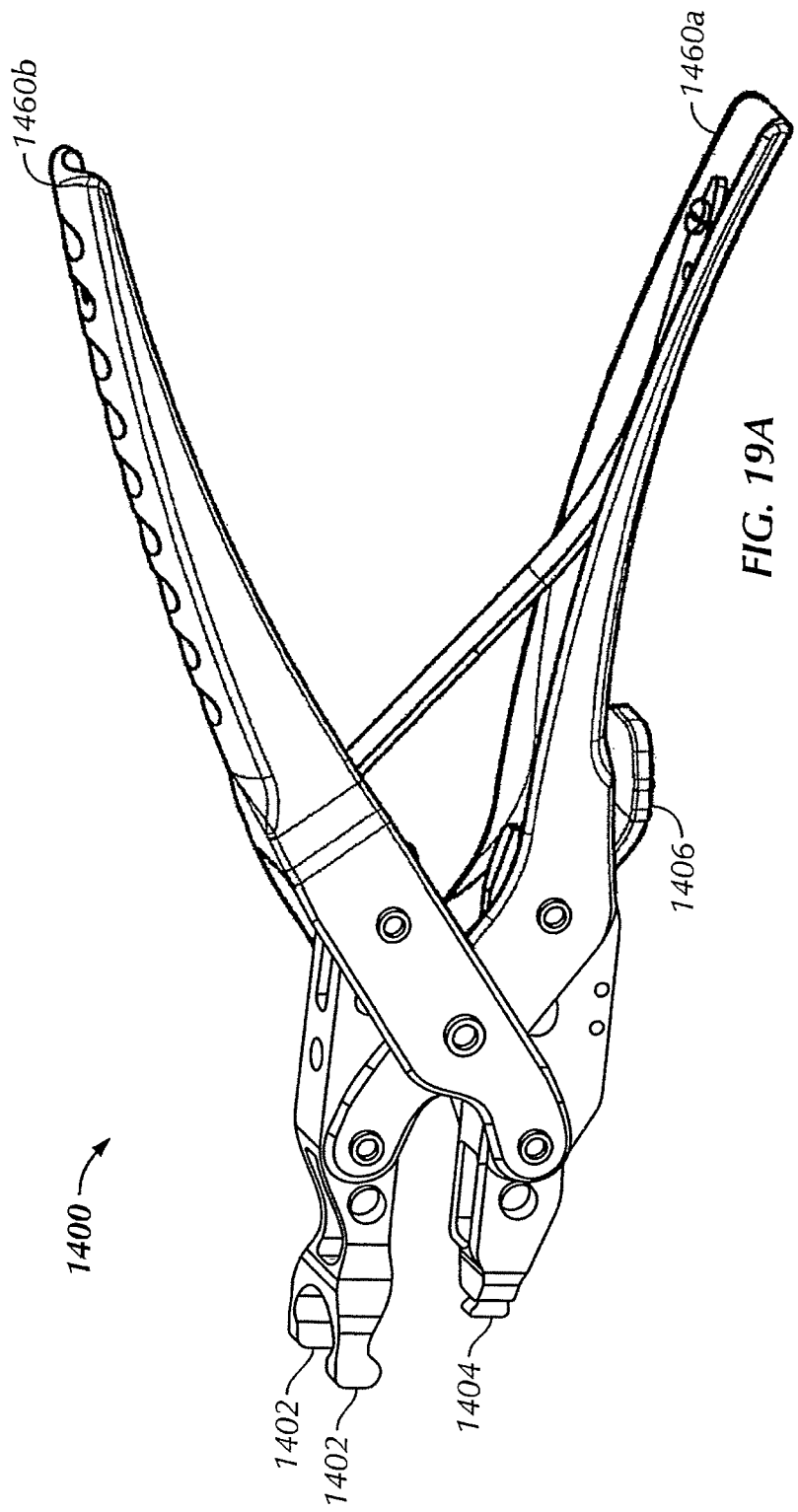
FIG. 19A is a side perspective view of a scissor persuader in accordance with the exemplary embodiment of the instrument set.
Figure 19B:
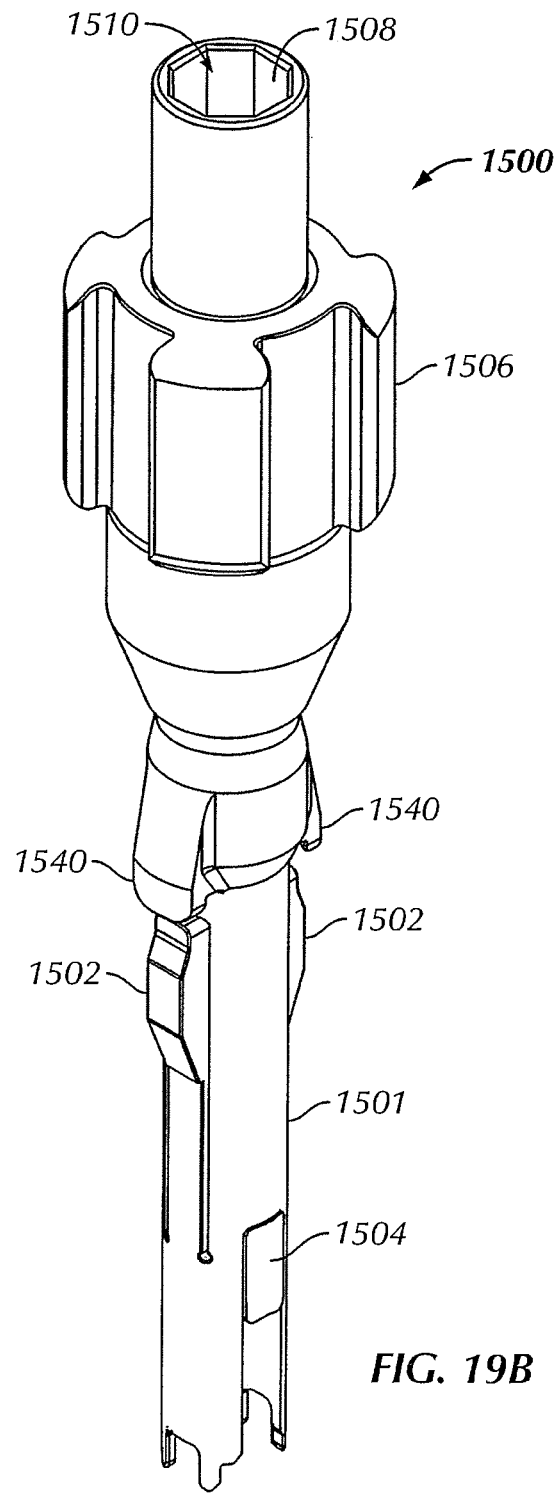
FIG. 19B is a side perspective view of a threaded persuader in accordance with the exemplary embodiment of the instrument set.
Figure 20:
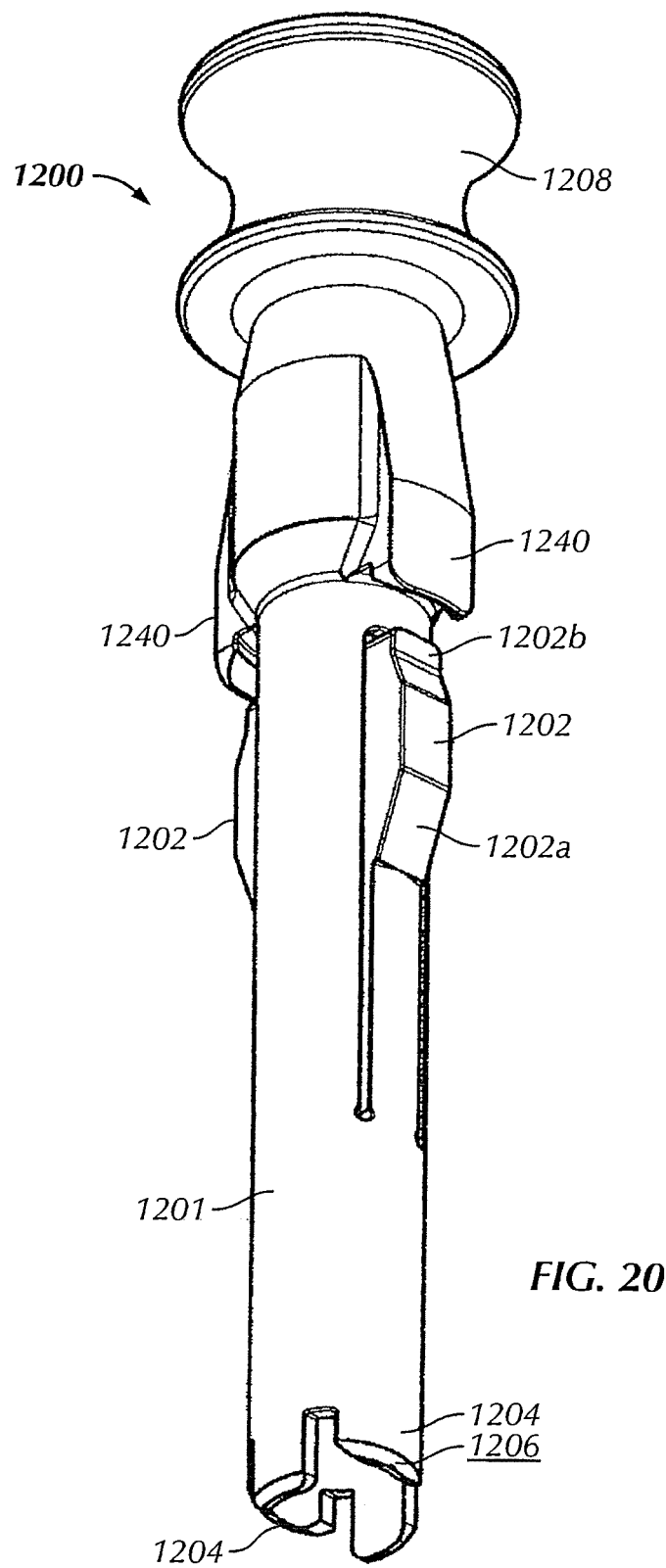
FIG. 20 is a side perspective view of a removal tool in accordance with the exemplary embodiment of the instrument set.
Figure 21A:
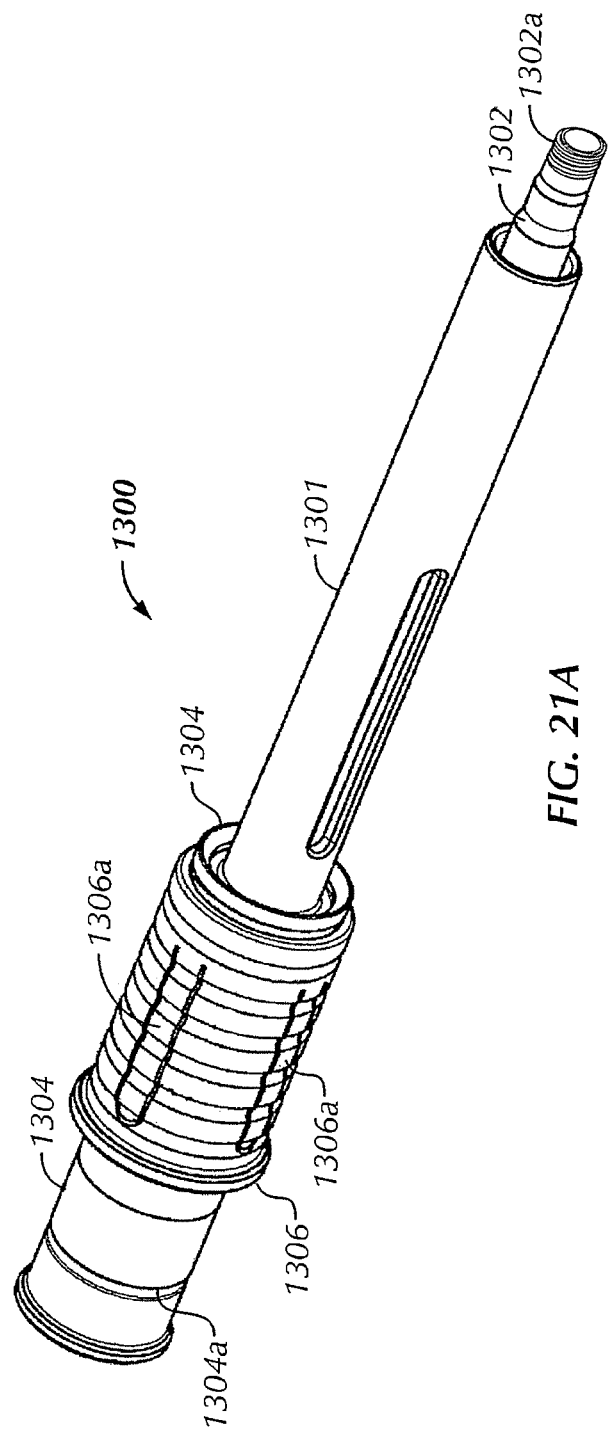
FIG. 21A is a side perspective view of a screw holder in accordance with the exemplary embodiment of the instrument set.
Figure 21B:
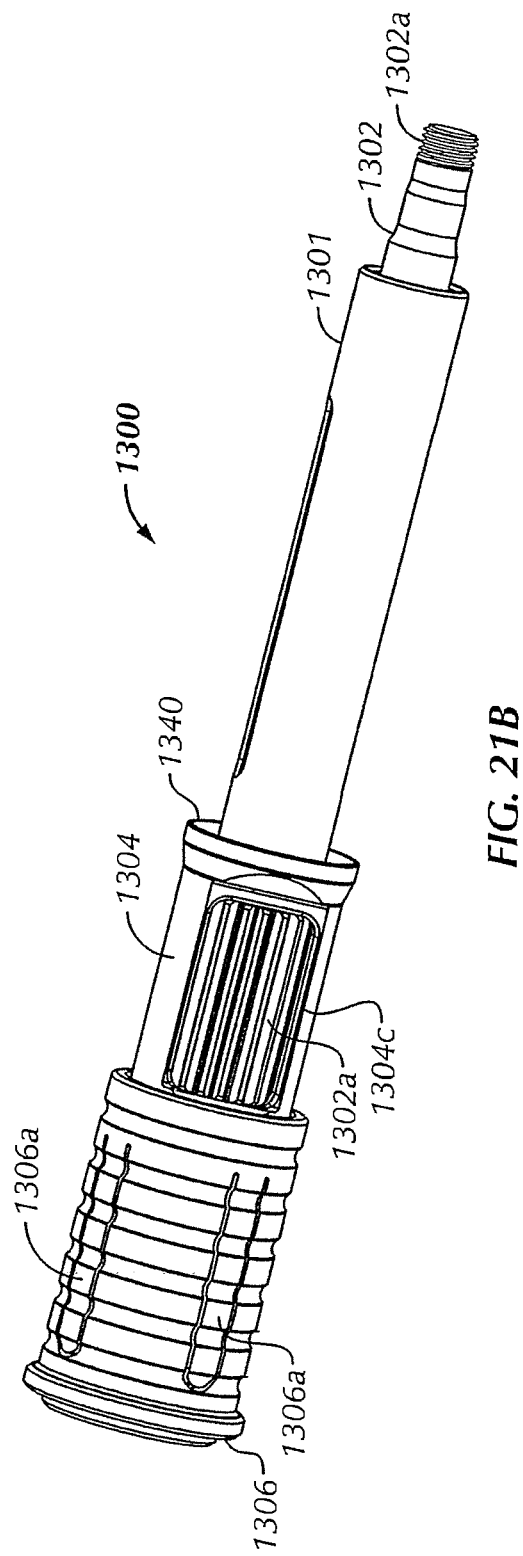
FIG. 21B is a side perspective view of the screw holder of FIG. 21A with a safety shield in an actuating position.
Figure 22:
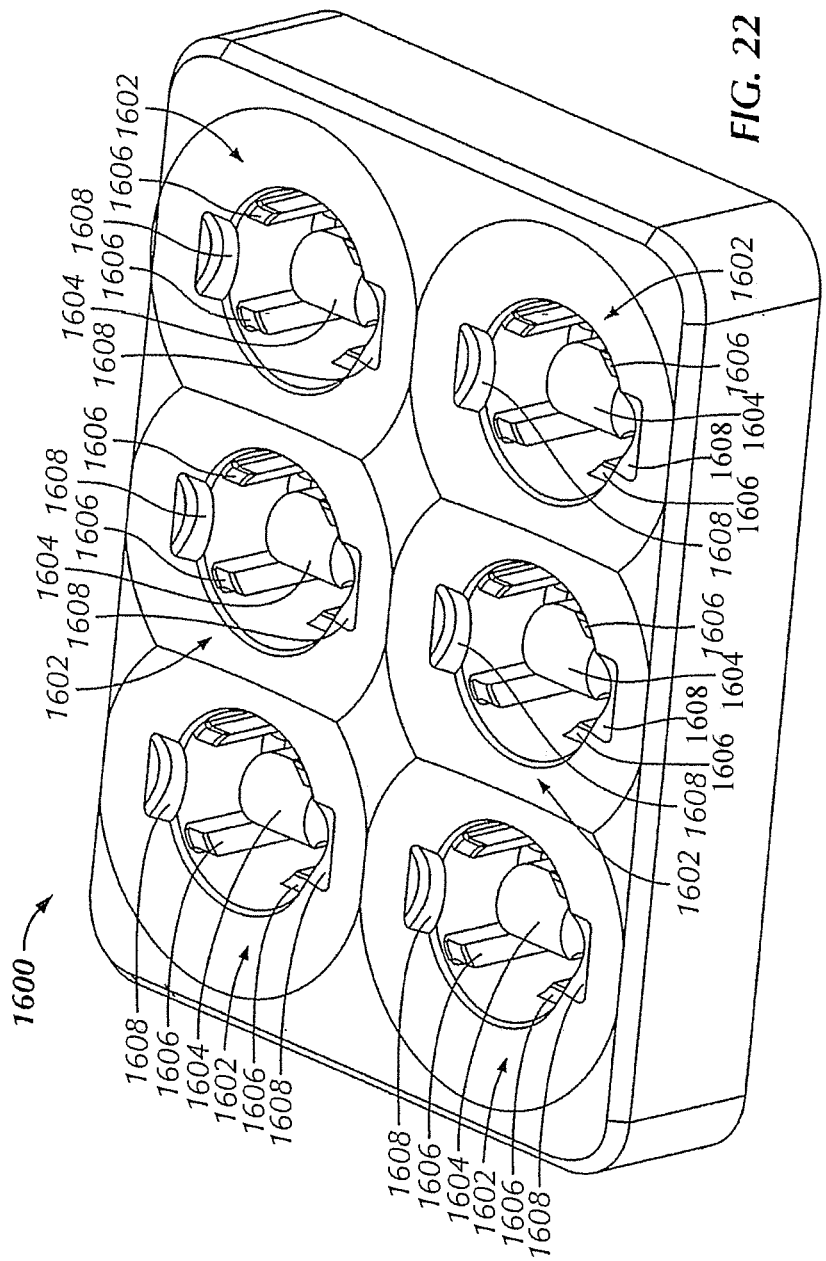
FIG. 22 is a top perspective view of a cap tray for holding several of the locking caps of FIG. 11 in accordance with the exemplary embodiment of the instrument set.

The cap guide 400 is configured to be removably couplable to the tissue retractor 200 within the partial pathway 206 such that the partial pathway 206 and the hollow cavity 406 are coaxially aligned and the longitudinal tissue retractor axis L-L and the longitudinal guide axis G-G are coaxial (FIG. 8). At least one slot 410 is formed at the distal end portion 402 of the cap guide 400 that extends generally longitudinally along a portion thereof. The slots 410 are defined by arms 422 that extend distally from the sleeve 401. Each arm 422 includes an arched cavity 424 for contacting the rod R (FIG. 19) during insertion of the locking cap 700 and concurrent reduction of the rod R into the rod slot 108 of the body 102. The slot 410 is aligned with one of the resiliently movable arms 210 when the cap guide 400 is coupled to the tissue retractor 200. The cap guide 400 is relatively stiff and strong, particularly when compared to the tissue retractor 200, to react loads encountered by the cap guide 400 when final tightening the locking cap 700 to the body 102. The relatively stiff and strong cap guide 400 is also able to limit damage to other components of the exemplary instrument set, such as the tissue retractor 200, the body 102, the locking cap 700 or any of the other components of the exemplary instrument set during final tightening by reacting the relatively high loads during final tightening. The greatest loads and stresses encountered by the cap guide 400 and the other components of the exemplary instrument set is during final tightening and the cap guide 400 is constructed to withstand this loading condition to protect the other components of the exemplary instrument set, certain of which are designed to maximize a surgeons line-of-sight and subsequently have comparatively lower stiffness and strength. Thus, the cap guide 400 is expected to be present in the incisions I, CI during portions of the procedure when the stiff, strong construction is required to react the final tightening forces rather than during those portions of the procedure when increased visibility is more desirable than increased strength.

The cap guide 400 also includes two indicia 432 at the proximal end portion 404 that are in alignment with the arched cavities 424 at the distal end portion 402. The indicias 432 provide a visual indication to a surgeon for aligning the arched cavities 424 with the rod R while inserting the locking cap 700 into the body 102 and the cap guide 400 into the partial pathway 206 to ensure that the arched cavities 424 engage and urge the rod R into the U-shaped rod slot or channel 108 of the body 102. Visually aligning the arched cavities 424 with the rod R during surgery without the indicias 432 could be difficult for a surgeon, because the cap guide 400, the tissue retractor 200 and the patients soft tissue T are typically blocking the surgeons line-of-sight to the surgical site in the minimally invasive procedure. The indicias 432 also assist in aligning a saddle portion 704 of the locking cap 700 with the rod R when the locking cap 700 is engaged with the cap guide 400. A compressor 1100, a distractor 1000, a remover or removal tool 1200, a holder 1300 or other similar instruments that are introduced into the partial pathway 206 may include similar indicia at their proximal end portions to assist a surgeon in properly aligning the instruments with the construct at the surgical site.

Figure 9:
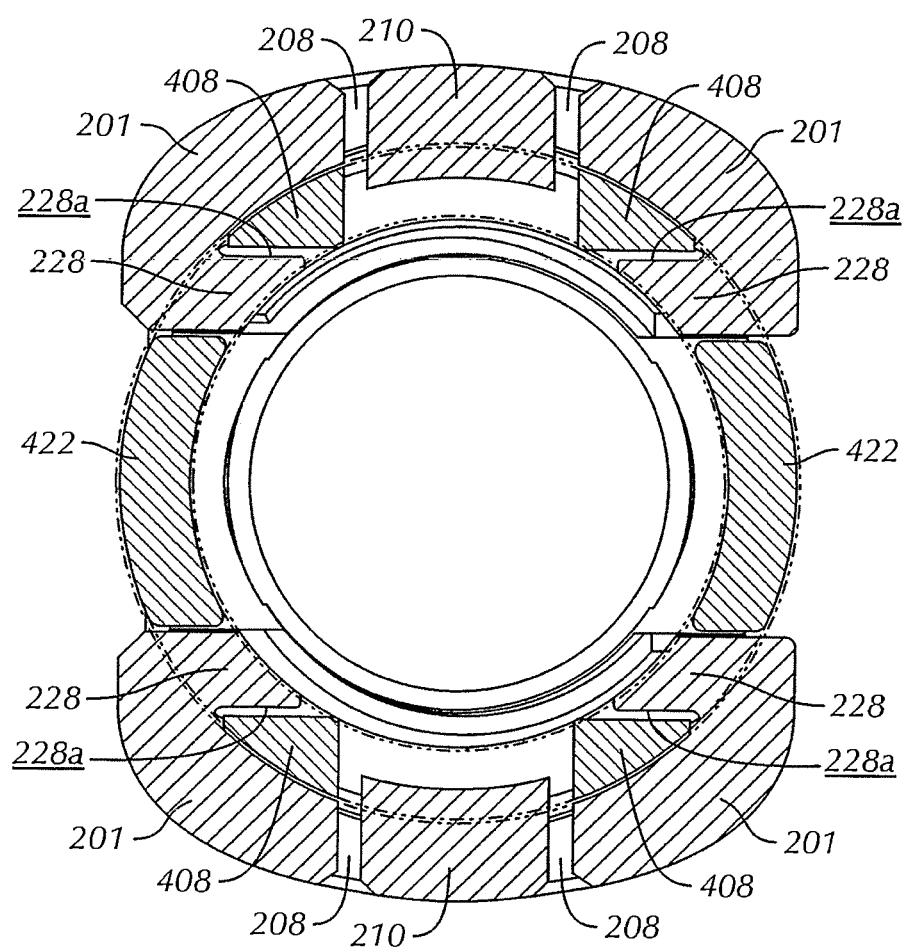
FIG. 9 is an enlarged cross-sectional view of the cap guide instrument of FIG. 6A coupled to the tissue retractor of FIG. 3, taken along line 9-9 of FIG. 8 with only portions of the cap guide instrument and tissue retractor shown for clarity.

The cap guide 400 further includes at least one, and typically four, blocking tabs 408 proximate the distal end portion 402. When coupled to the tissue retractor 200, the blocking tabs 408 are received by at least one, and typically four, blocking ribs 228 of the tissue retractor 200 (FIG. 9). The blocking tabs 408 typically contact inner surfaces 228*a* of the corresponding blocking ribs 228 in the presence of a force exerted by the bone screw 100 on the inner surface 201*a* of the tissue retractor 200. The blocking ribs 228 are generally positioned close to the screw engagement ribs 214 in the relatively narrow bulky section at the distal end portion 202 of the tissue retractor 200. Accordingly, any final tightening forces reacted by the tissue retractor 200 flow from the body 102 through the screw engagement ribs 214, through a short or narrow bulked-up portion 203 of the tissue retractor 200 at the distal end portion 202, through the blocking ribs 228 and directly into the strong, stiff cylindrical sleeve 401 of the cap guide 400. Accordingly, the forces of final tightening are essentially shielded form the relatively thin tissue retractor 200 by immediately directing the forces into the cap guide 400 by transferring the forces through the short bulked upon portion 203 of the tissue retractor 200 at the distal end portion 202. The cap guide 400 therefore limits splay of the body 102 of the polyaxial bone screw 100 and the tissue retractor 200 during insertion of the locking cap 700.

A gap may be defined between the blocking tabs 408 and the inner surfaces 228a of the corresponding blocking ribs 228 (FIG. 9) to accommodate sliding insertion of the cap guide 400 into the tissue retractor 200 by providing clearance for insertion of the blocking tabs 408 into the gap between the blocking ribs 228 and the body 201 of the tissue retractor 200. The gap is relatively small to limit splay of the tissue retractor 200 and the body 102 when the assembly is subjected to final tightening forces.

A guide button 426 extends radially outwardly from a side of the cylindrical sleeve 401 proximate the distal end portion 402. The guide button 426 has a button width $W_B$ that is slightly smaller than a slot width $W_S$ (FIG. 4) of the second slot 218b. The guide button 426 also includes relatively smooth, arcuate corners 428, particularly on a distal end portion. When inserting the cap guide 400 into the partial pathway 206 of the tissue retractor 200, the guide button 426 self-guides and orients the cap guide 400 into proper alignment with the tissue retractor 200. For example, if the cap guide 400 is introduced into the partial pathway such that the guide button 424 initially contacts the second longitudinal, helix-shaped edge 226, the guide button 424 slides down the second helix-shaped edge 226 until the guide button 426 drops into the second slot 218b. When the guide button 426 is positioned in the second slot 218b in the assembled configuration, the arched cavities 424 and the indicias 432 are aligned with the rod R and the blocking tabs 408 are positioned between the blocking ribs 228 and the body 201, generally at four locations, to limit splay of the tissue retractor 200 and the body 102. In addition, the guide button 426, the arms 422 and the blocking tabs 408 may cooperate to secure the cap guide 400 relative to the tissue retractor 200 in five of six degrees of freedom, with the exception being the movement of the cap guide 400 out of the partial pathway 206 along the longitudinal tissue retractor axis L-L away from the distal end portion 202 of the tissue retractor 200.

Anti-splay wings 440 extend radially outwardly from the sleeve 401 near the proximal end portion 404 and define a capture groove 442 between the sleeve 401 and a distal wing end portion 440a. In the assembled configuration, when the cap guide 400 is positioned in the partial pathway 206 with the blocking tabs 408 located between the blocking ribs 228 and the body 201, the terminal portion 204a at the proximal end portion 204 of the tissue retractor 200 is positioned within the capture groove 442 to limit outward splay of the proximal end portion 204 during use. The two anti-splay wings 440 may be utilized, for example, with the two-piece retractor 300 to engage the proximal end portions of the first and second tissue retractors 300a, 300b, respectively.

The cap guide 400 also typically includes clearance windows 450 and capture grooves 460 on either side near the proximal end portion 404. The clearance windows 450 and the capture grooves 460 are utilized with additional instruments of the exemplary instrument set to manipulate or align the cap guide 400 with other instruments, which will be described in greater detail below.

Referring to FIGS. 8 and 11, a screwdriver 500 may be utilized with the polyaxial bone screw 100, tissue retractor 200 and cap guide 400 assembly for threadably securing the locking cap 700 (FIG. 12) onto the body 102 of the polyaxial bone screw 100. The screwdriver 500 includes a handle 502 and a drive shaft 504 extending therefrom. The drive shaft 504 has a diameter that is less than a diameter of the hollow cavity 406 within the cap guide 400. Accordingly, the drive shaft 504 is rotatable with respect to the cap guide 400 when positioned therein. The drive shaft 504 has a terminal end portion (not shown) which is configured to mate with a drive feature 701 on top of the locking cap 700 in a releasable, rotatably fixed fashion.

Referring to FIGS. 6A-8, a counter-torque handle 600 has a gripping end portion 602 and an interlock end portion 604. The interlock end portion 604 includes an instrument interface 606 that is releasably positionable within the hollow cavity 406 at the proximal end portion 404 (FIG. 6B). When inserted into the hollow cavity 406, the instrument interface 606, and consequently the counter-torque handle 600, are rotatably fixed with respect to the cap guide 400. The instrument interface 606 includes a generally smooth inner surface 606a and at least one spline 606b on an external surface that mates with a complementary spline 412 in the hollow cavity 406 at the proximal end portion 404 of the cap guide 400. The at least one spline 606b and the complementary spline 412 may be comprised of an octagonal spline or a spline having eight sides that are configured to align the gripping end portion 602 with the indicias 432 and the rod R, are positioned perpendicular to the indicias 432 and the rod or are oriented at forty-five degrees (45°) relative to the indicias 432 and the rod R. Accordingly, the surgeon may orient the gripping end portion 602 generally perpendicular to the surgeon, generally pointing away from the surgeon, generally pointing toward the surgeon or oriented at forty-five degrees (45°) toward and/or away from the surgeon. Such orientations permit the counter-torque handle 600 to be adaptable to left and right handed surgeons, to grasping by assistants and/or generally for surgeon comfort. The surgeon may utilize these various orientations for comfort or for an assistant to hold the counter-torque handle 600. The spline 606b and complementary spine 412 may also be configured to have nearly any number of sides that are divisible by four (4), for example, square splines such that the surgeon has at least four orientations to position the counter-torque handle 600 relative to the cap guide 400 or other instrument.

The interlock end portion 604 further includes an open-ended slot 610 having a width greater than the diameter of the drive shaft 504. The drive shaft 504 is therefore not only rotatable within the open-ended slot 610 of the counter-torque handle 600, but the counter-torque handle 600 is insertable and removable from the cap guide 400 while the drive shaft 504 is within the hollow cavity 406 of the cap guide 400 and while the cap guide 400 is within the partial pathway 206 of the tissue retractor 200. Accordingly, insertion, tightening, and counter-torque operations of the locking cap 700 can be performed without excessive removal and replacement of instruments and the counter-torque handle 600 can be engaged with the cap guide 400 when it is required for final tightening. In addition, the solid engagement provided between the counter-torque handle 600 and the body 102 of the polyaxial pedicle screw 100 is relatively stiff and strong because of the arrangement of the tissue retractor 200 and the cap guide 400 and their engagement with each other and the body 102. Specifically, final tightening loads are generally shielded from the tissue retractor 200, except at the bulked-up portion 203 between the screw engagement ribs 214 and the blocking ribs 228 at the distal end portion 202 where the tissue retractor 200 includes extra strength and stiffness to react the load. Accordingly, the instrumentation necessary for final tightening, including the tissue retractor 200, the cap guide 400 and the counter-torque handle 600, is positioned at least near the generally conical incision CI during the final tightening procedure and may be quickly removed and adapted during alternate steps of the procedure. The cap guide 400 is not specifically necessary for final tightening of the construct, as final tightening may also be performed with the distractor 1000, the compressor 1100, a threaded persuader 1500 or other related instrument that engages the body 102, receives the screwdriver 500 and counter-torque handle 600 and is able to retain the locking cap 700.

The instrument interface 606 may also be configured such that the at least one spline 606*b* is defined in the inner surface 606*a* for grasping the complementary spline 412 on the external surface of the cap guide 400 (not shown). Such a configuration permits the open-ended slot 610 to accommodate quick engagement and release of the counter-torque handle 600 with the cap guide 400 without removal of the screwdriver 500 or other instruments from the incision I.

Referring now to FIG. 11, the locking cap 700 is typically constructed of titanium or a titanium alloy, such as an alloy including Titanium, Aluminum and Niobium (TAN—TI-6Al-6Nb—ASTM F 1295) but may also be constructed of stainless steel, other metallic alloy materials or nearly any strong, stiff, biocompatible material that is able to take on the general size and shape of the locking cap 700 and withstand the normal operating conditions of the locking cap 700. The locking cap 700 includes a threaded portion 702 and the saddle 704 rotatably mounted to the threaded portion 702. The saddle 704 is generally machined with a post (not shown) that mates with an axial hole (not shown) in the threaded portion 702 and is rotatably secured thereto. The locking cap 700 is generally shown in WO 100 and is not limited to constructions including the saddle 704 and the threaded portion 702. For example, the locking cap 700 may be comprised of nearly any style or variety of locking cap that is known to those having ordinary skill in the art. The threaded portion 702 includes a plurality of threads 712 that mate with the threaded portions 114 of the inner surfaces 110*a* of the arms 110 of the body 102 in the polyaxial bone screw 100. The saddle portion 704 includes two downwardly extending arms 706, 708 that form an arched cavity 710 therebetween. The saddle 704 includes a grooved surface 704*a* that assists in securing the saddle 704 to the rod R in the implanted and locked position. The cavity 710 is sized and shaped to complementarily receive the rod R when the locking cap 700 is mounted in the polyaxial bone screw 100.

Referring to FIGS. 6A, 6B, 11 and 18, the locking cap 700 is removably insertable into a distal end portion of the hollow cavity 406 of the cap guide 400 and the saddle 704 is rotatable with respect to the cap guide 400 and the threaded portion 702 when the locking cap 700 is secured to the cap guide 700. To accommodate the locking cap 700, the exemplary cap guide 400 includes a movable cap tab 414 (FIG. 18), located proximate the distal end portion 402 of the cap guide 400 and projecting into the hollow cavity 406. The cap tab 414 is disposed at a distal end portion 418 of a resiliently movable arm 416 of the cap guide 400 (FIG. 6). The movable arm 416 is attached at a proximal end portion 420 thereof to the sleeve 401 of the cap guide 400. The cap tab 414 may alternatively be comprised of a portion of thread (not shown) that projects into the hollow cavity 406 to engage the threaded portion 702 of the locking cap 700 and secure the locking cap 700 to the distal end portion 402 of the cap guide 400. Further, the cap guide 400 may include additional alternative mechanisms to temporarily secure the locking cap 700 in the hollow cavity 406 of the cap guide 400, such as hook and loop material, adhesive materials, clamps, releasable fasteners or like mechanisms.

In the exemplary embodiment, the movable arm 416 is constructed of a spring steel material and is welded at a proximal peripheral edge 416*a* to the cap guide 400. A gap 416*b* is defined between the movable arm 416 and the cap guide 400 at a distal periphery of the movable arm 416 such that the distal end portion 418 of the movable arm 416 may flex to receive and release the locking cap 700 during insertion and removal of the locking cap 700, respectively, from the hollow cavity 406. The locking cap 700 is prevented from being over-inserted into the hollow cavity 406 by a narrowed portion 409 (FIG. 18) of the cap guide 400 that extends radially inwardly into the hollow cavity 406 proximate the distal end portion 402 and abuts a top surface 702*a* of the locking cap 700 to align a longitudinal cap axis C-C with the longitudinal guide axis G-G of the cap guide 400. The cap tab 414 is received in threads 712 of the threaded portion 702 of the locking cap 700 when the locking cap 700 is inserted and secured in the hollow cavity 406 of the cap guide 400 in the assembled configuration.

With the locking cap 700 in the hollow cavity 406 of the cap guide 400, the cap guide 400 is positioned within the tissue retractor 200 such that the partial pathway 206 and the hollow cavity 406 are coaxially aligned and the locking cap 700 is coaxially aligned with the body 102 of the polyaxial bone screw 100. In this assembled configuration, the longitudinal cap axis C-C is generally coaxial with the longitudinal tissue retractor axis L-L and the longitudinal guide axis G-G. This configuration permits mating of the threaded portion 702 of the locking cap 700 with the threaded portions 114 of the body 102 without cross-threading or the like because the alignment of the cap guide 400 and cap screw 700 automatically provides vertical alignment of the threaded portion 702 of the locking cap 700 with the threaded portions 114 of the body 102 when the cap guide 400 is properly locked in position within the tissue retractor 200 (FIG. 8). The drive shaft 504 of the screw driver 504 is also preferably coaxially aligned with the longitudinal tissue retractor axis L-L, the longitudinal guide axis G-G and the longitudinal cap axis C-C in this assembled configuration (FIG. 8).

Referring to FIGS. 6A, 6B, 8 and 12-14, other instruments such as the compressor 1100, the distractor 1000, the removal tool 1200, the holder 1300 or the like may be used in conjunction with the exemplary instrument set that also limit splay, cross-threading, and other unfavorable consequences of insertion and final tightening of the locking cap 700 to lock the rod R in the polyaxial bone screw assembly 100 and the bone screw 104 relative to the body 102. For example, the compressor 1100 and/or the distractor 1000 have many similar structural features to that of the cap guide 400, particularly at their distal end portions to engage the tissue retractor 200 and the locking cap 700. Accordingly, like numerals have been used for like elements, except the 1000 series numerals have been used to identify features of the distractor 1000 and 1100 series numerals have been used to identify features of the compressor 1100. Accordingly, a complete description of the exemplary embodiment of the compressor 1100 and the distractor 1000 have been omitted, with only the notable differences being described. The compressor 1100 and the distractor 1000 include many of the features of the cap guide 400 while retaining their specific features that permit distraction and compression between adjacent polyaxial bone screws 100, which are apparent to those having ordinary skill in the art, for the function of the compressor 1100 and the distractor 1000. Accordingly, although the cap guide instrument 400 is described in this application for performing a number of functions during spine surgery, the compressor 1100 and the distractor 1000 or other similar instruments may be substituted therefore, when appropriate.

Figure 12:
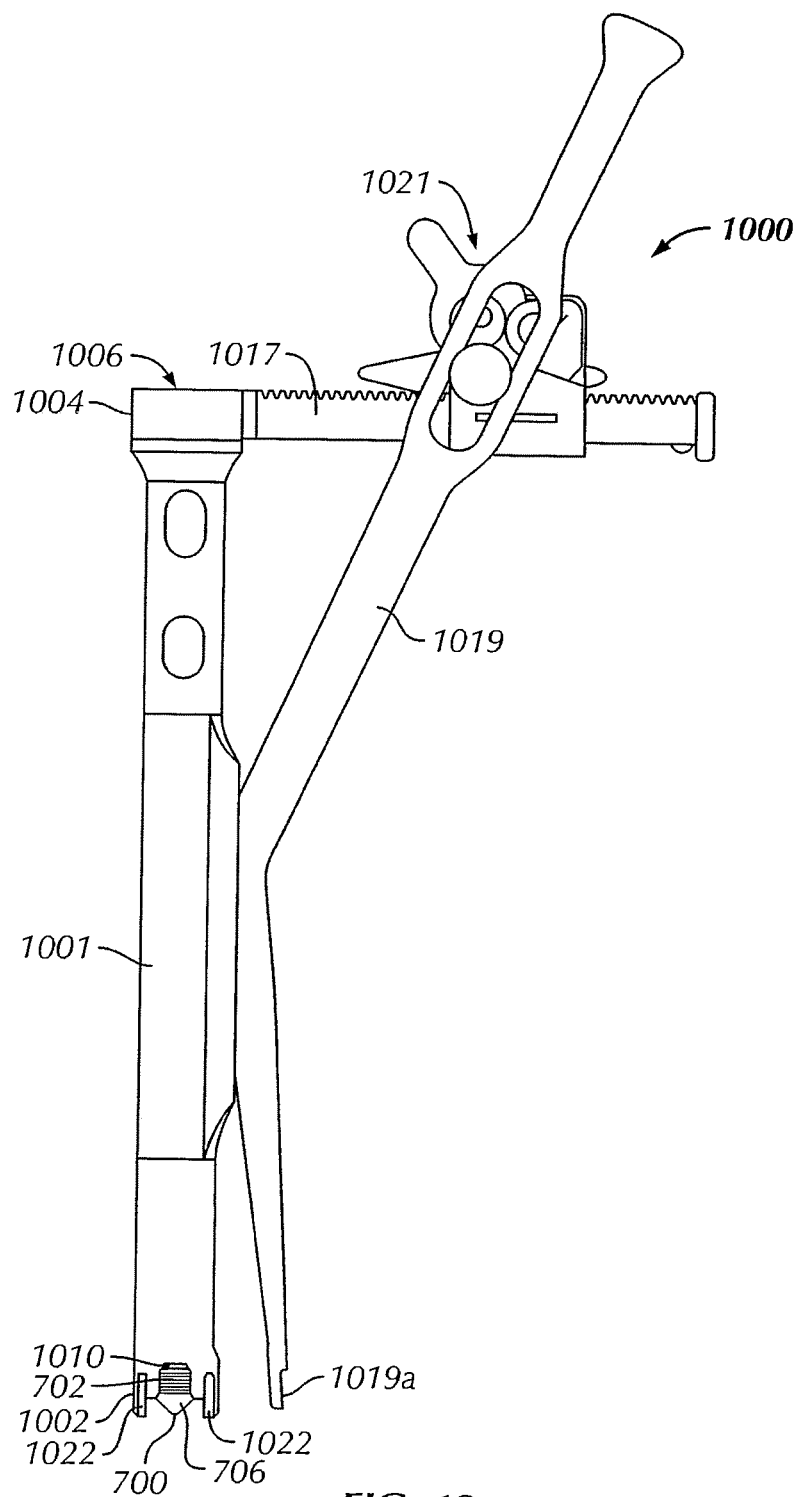
FIG. 12 is a front elevational view of a distractor in accordance with the exemplary embodiment the instrument set with the locking cap of FIG. 11 mounted therein.
Figure 13:
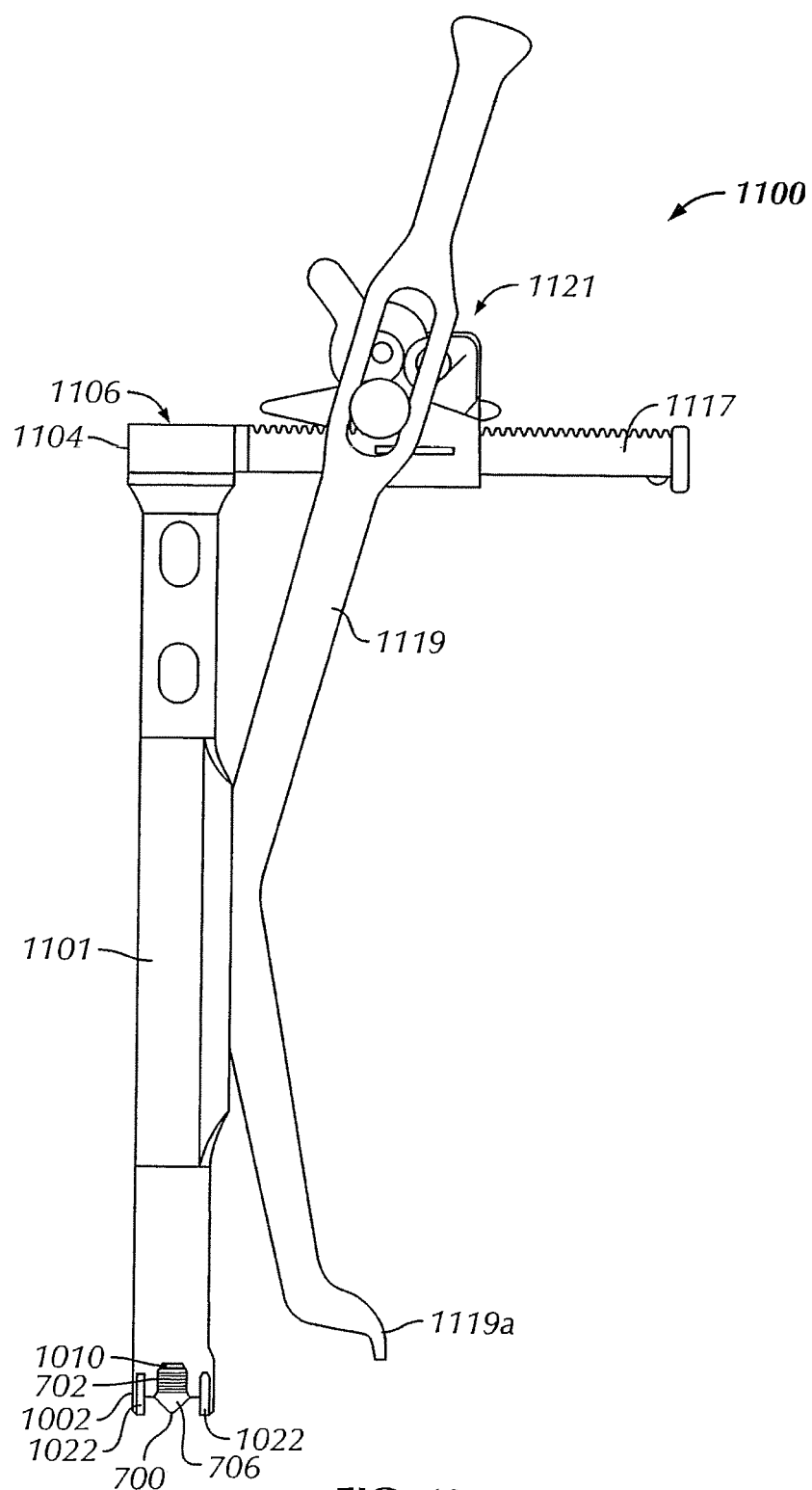
FIG. 13 is front elevational view of a compressor in accordance with the exemplary embodiment the instrument set with the locking cap of FIG. 11 mounted therein.
Figure 14:
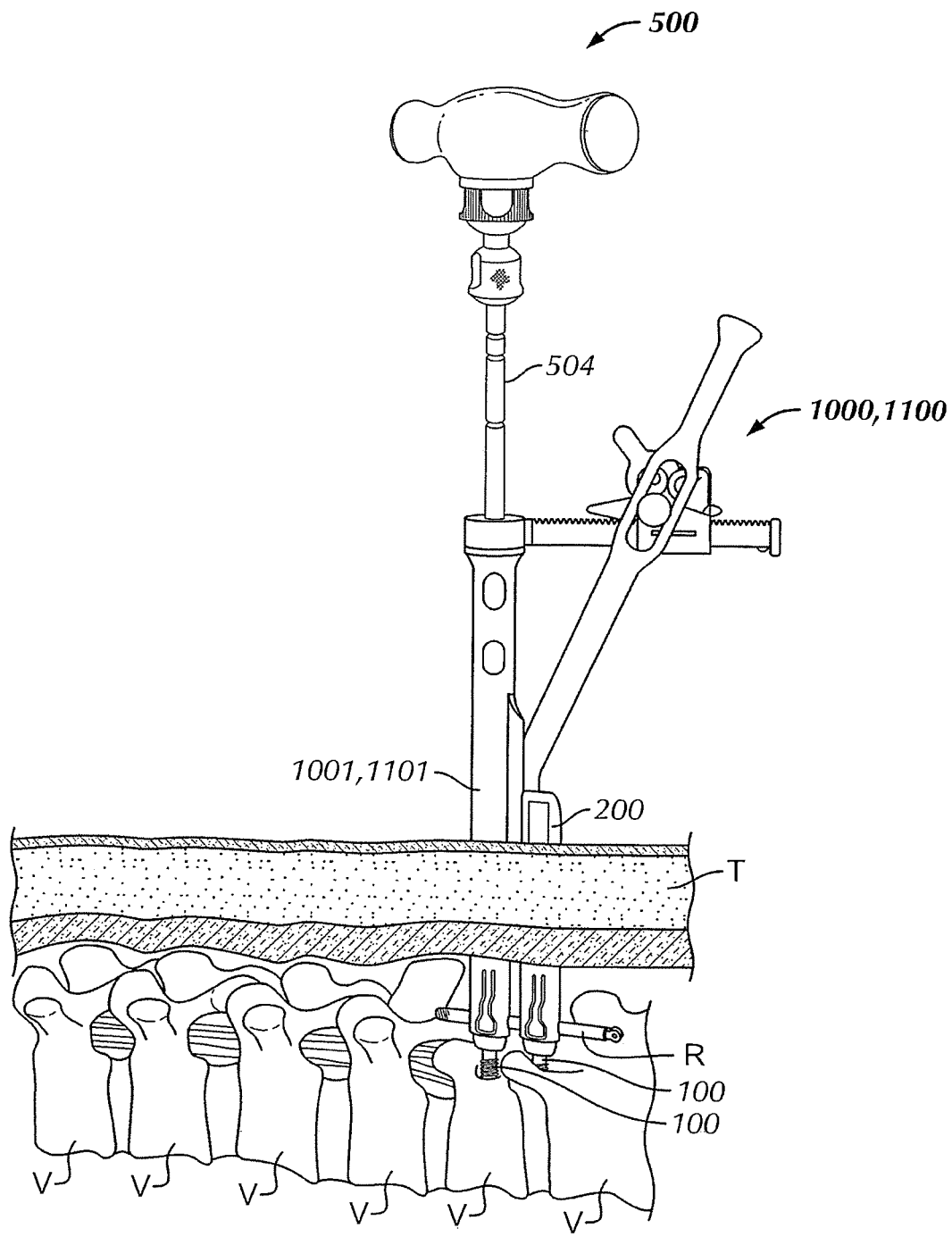
FIG. 14 is a side elevational view of pedicle screws of FIG. 1 and tissue retractors of FIG. 11 further including the distractor or compressor of FIG. 12 or 13, a rod, and a screwdriver in accordance with the exemplary instrument set arranged for a surgical procedure.
Figure 15:
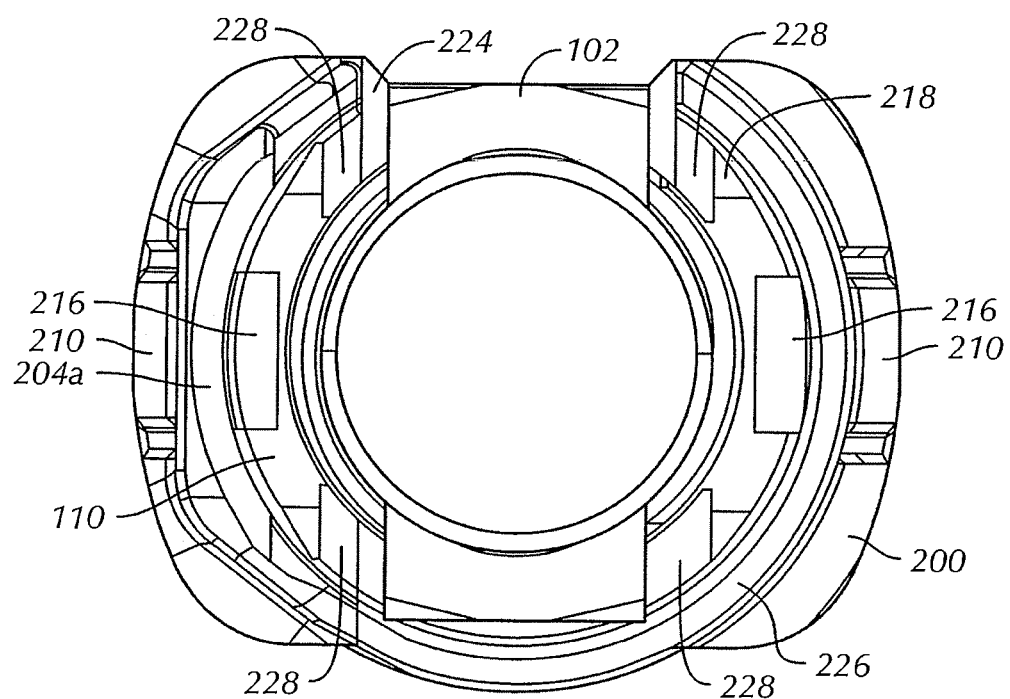
FIG. 15 is a greatly enlarged top plan view of a body of the polyaxial bone screw of FIG. 1 coupled to the tissue retractor of FIG. 3.
Figure 18:
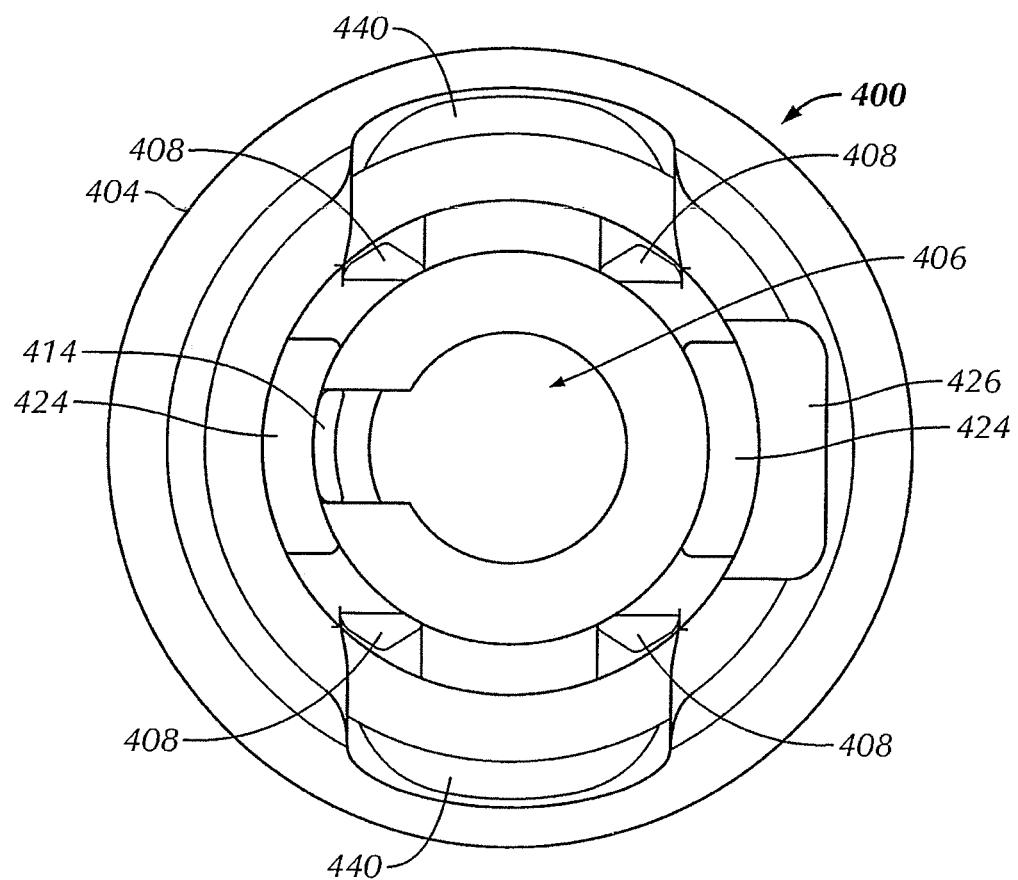
FIG. 18 is a greatly enlarged bottom plan view of the cap guide instrument of FIG. 6.

Referring to FIGS. 12-14, the distractor 1000 and the compressor 1100 both include a ratchet arm 1017, 1117, a pivoting arm 1019, 1119 that is pivotally mounted to the cylindrical sleeve 1001, 1101 and a ratchet mechanism 1021, 1121 that can be used to lock the pivoting arm 1019, 1119 relative to the cylindrical sleeve 1001, 1101 or mechanically move the pivoting arm 1019, 1119 relative to the cylindrical sleeve 1001, 1101. The distractor 1001 includes a blunt end portion 1019a at the distal end portion of the pivoting arm 1019 and the compressor 1100 includes a hooked end portion 1119a at the distal end portion of its pivoting end 1119. In use, the blunt end 1019a of the distractor 1000 abuts a side surface of the locking cap 700 of an adjacent polyaxial screw 100 while the cylindrical sleeve 1001 is secured to the other polyaxial screw 100 and the screws 100 are urged away from each other, typically to relief pressure on nerves between two adjacent vertebrae V. In contrast, the hooked end portion 1119a of the compressor 1100 extends through the first and second slots 218a, 218b of the tissue retractor 200 opposite the screw 100 that the cylindrical sleeve 1101 is attached to. The hooked end 1119a engages the locking cap 700 of this screw 100 and urges the polyaxial screws 100 and adjacent vertebrae V toward each other to compress the vertebrae V together or against a spacer S (FIG. 10C) positioned between the vertebrae V.

Referring to FIGS. 3-6B, 8 and 19A, the exemplary instrument set of the present application includes a scissor persuader 1400 having groove engaging arms 1402 attached to a first hand grip 1460a, a window engaging nose 1404 secured to a second hand grip 1460b and a release tab 1406. When a polyaxial screw 100 has been inserted into the vertebrae V with the tissue retractor 200 mounted thereto, the rod R is positioned in the rod slot 108 and the cap guide 400 with the locking cap 700 secured at the distal end portion 402 of the cap guide 400 is positioned in the partial pathway 206, the rod R may be difficult to fully seat in the rod saddle 101a in certain situations. In addition, it may be difficult for the surgeon to urge the rod R far enough into the rod slot 108 to initially engage the threads 712 of the threaded portion 702 with the threaded portions 114 of the arms 110 with only hand or manual force. The scissor persuader 1400 may be utilized to apply mechanical force to urge the cap guide 400 downwardly within the partial pathway 206 of the tissue retractor 200 to urge the rod R into the rod slot 108 and/or the threads 712 of the threaded portion 702 into engagement with the threaded portions 114 of the arms 110.

In use, the groove engaging arms 1402 are positioned in the grasping grooves 460 and the window engaging nose 1404 is engaged with a proximal end of the window 230 of the tissue retractor 200. The first and second handle grips 1460a, 1460b are squeezed together to urge the groove engaging arms 1402 toward the window engaging nose 1404 and the cap guide 400 further into the partial pathway 206 of the tissue retractor 200. Urging the cap guide 400 downwardly causes the locking cap 700 to urge the rod R downwardly into the rod slot 108. The scissor persuader 1400 may be utilized without blocking insertion of the drive shaft 504 of the screwdriver 500 into the hollow cavity 406 and into engagement with the drive feature 701 of the locking cap 700. In addition, the scissor persuader 1400 does not block engagement of the counter-torque handle 600 with the cap guide 400. When the cap guide 400 has been persuaded to the assembled or working configuration relative to the tissue retractor 200, the persuader 1400 locks in position such that the surgeon does not have to continue to hold the first and second hand grips 1460a, 1460b to maintain the position of the cap guide 400 relative to the tissue retractor 200. To release the lock of the scissor persuader 1400, the release tab 1406 is actuated and the scissor persuader 1400 may be removed from engagement with the cap guide 400 and the tissue retractor 200. The position of the clearance window 450 in alignment with the window 230 of the tissue retractor 200 provides clearance for the window engaging nose 1404 in operation.

Referring to FIGS. 1-8 and 19B, a threaded persuader 1500 may be utilized to similarly persuade the rod R into the rod slot 108, typically in situations where the travel of the scissor persuader 1400 is insufficient to persuade the rod R. The threaded persuader 1500 includes spring arms 1502 on opposing sides, a slider 1504 that releasably engages the locking cap 700 in a similar manner to the above-described cap guide 400, a hand actuator 1506 at a proximal end of the threaded persuader 1500 to move the slider 1504 relative to the cylindrical sleeve 1501, anti-splay wings 1540 and an internal spline 1508 to engage the spline 606b of the counter-torque handle 600.

In use, if the rod R is positioned proud of the rod slot 108 a sufficient distance that the scissor persuader 1400 is unable to engage the cap guide 400 and the tissue retractor 200 to persuade the rod R or the scissor persuader 1400 is unable to apply enough force to persuade the rod R, the threaded persuader 1500 may be introduced into the partial pathway 206 and engage the tissue retractor 200 proximate the distal end portion 202 in a similar manner to the cap guide 400. When fully assembled and seated in the tissue retractor 200, the spring arms 1502 spring outwardly into the windows 230 or a single window 230 of the tissue retractor 200 to translatably secure the threaded persuader 1500 relative to the tissue retractor 200 and the polyaxial screw 100 along the longitudinal tissue retractor axis L-L. The hand actuator 1506 is rotated relative to the cylindrical sleeve 1501 such that the slider 1504 moves downwardly toward the distal end and the saddle 704 engages the rod R. Further pivoting of the hand actuator 1506 urges the slider 1504 further toward the distal end and persuades the rod R into the rod slot 108 and the threads 712 of the threaded portion 702 into engagement with the threaded portions 114 of the arms 110. The urging forces of pushing the rod R into the rod slot 108 are reacted through the tissue retractor 200 and into the cylindrical sleeve 1501 through the spring arms 1502. When the rod R is persuaded a sufficient amount to allow engagement of the threads 712 of threaded portion 702 with the threaded portions 114 of the arms 110, the drive shaft 504 of the screwdriver 500 is introduced through the hollow central channel 1510 of the threaded persuader 1500 to screw the locking cap 700 into the body 102. To remove the threaded persuader 1500 from the tissue retractor 200, the spring arms 1502 are urged inwardly out of the window 230 and the threaded persuader 1500 slides out of the partial pathway 206.

Referring to FIGS. 1-5, 10A-10C, 13, 14, 16, 17 and 20, to remove the tissue retractors 200, 300 from the polyaxial bone screw 100 or any other mechanism that engages the polyaxial bone screw 100 with a device similar to the resilient movable arms 210 of the tissue retractors 200, 300, the removal tool 1200 is utilized to actuate the resiliently movable arms 210 from the relaxed position to the flexed position. The removal tool 1200 includes a cylindrical sleeve 1201, spring arms 1202, actuating arms 1204 with ramped distal surfaces 1206, a handle 1208 and anti-splay wings 1240.

In use, after the polyaxial screws 100 are inserted in the vertebra V, the locking caps 700 have been final tightened and the cap guide 400, counter torque handle 600, screwdriver 500 and other components have been removed from the partial pathway 206, the removal tool 1200 is inserted into the partial pathway 206. The cylindrical sleeve 1201 has a diameter slightly smaller than an inner diameter of the tissue retractor 200 proximate the distal end portion 202. The cylindrical sleeve 1201 slides into the partial pathway 206 until one of the spring arms 1202 snap into the window 230, the window 330 or a related feature on other instruments of the exemplary instrument set to axially secure the removal tool 1200 to the tissue retractors 200, 300. In this position, the actuating arms 1204 engage the retaining tab 216, 316 to urge the resiliently movable arms 210, 310 to the flexed position, wherein the attachment tab 212, 312 is moved out of engagement with the recess 116 on the body 102. The ramped distal surfaces 1206 facilitate the flexing of the resilient movable arms 210, 310 outwardly to the flexed position. The anti-splay wings 1240, particularly with the first and second tissue retractors 300a, 300b, laterally retain the tissue retractors 200, 300 relative to the cylindrical sleeve 1201. The removal tool 1200 and the tissue retractor 200, 300 or related instruments may then be removed from the patients body out of the generally conical incision CI and through the skin incision I.

The spring arms 1202 typically include a ramped nose 1202a and a relatively squared or blunt butt end portion 1202b. The ramped nose 1202 facilitates engagement of at least one of the springs arms 1202 in the window 230 of the tissue retractor 200 as the cylindrical sleeve 1201 of the removal tool 1200 slides into the partial pathway 206. The blunt butt end portion 1202b is generally positioned against or near a proximal end of the window 230 to inhibit sliding movement of the removal tool 1200 out of the partial pathway 206 once the spring arm 1202 is engaged with the window 230. The spring arms 1202 operate in a similar manner with respect to the windows 330 of the first and second tissue retractors 300a.

The windows 230, 330 may include a rough or uneven surface 230a, 330a proximate the windows 230, 330 on an outer surface of the bodies 201, 301. The rough or uneven surface 230a, 330a proximate the windows 230, 330 facilitate gripping and handling of the tissue retractors 200, 300 by surgeons and technicians in an operating environment. For example, the rough or uneven surface 230a, 330a permits a surgeon, who may have wet and slimy gloves on their hands, to grip the rough or uneven surface 230a, 330a with a thumb while urging the spring arm 1202 out of the window 230, 330 and sliding the removal tool 1200 out of the partial pathway 206, 306 of the tissue retractor 200, 300. The surgeon's wet and slimy finger may slip on the outer surface of the bodies 201, 301 without inclusion of the rough or uneven surface 230a, 330a. The rough or uneven surface 230a, 330a may be comprised of grooves, knurling, cavities, spikes, surface roughenings or other like features.

Referring to FIGS. 1-5, 16, 17, 21A and 21B, a holder 1300 is utilized to hold the polyaxial screw 100 and tissue retractors 200, 300 to drive the polyaxial screws 100 into the vertebrae V. The holder 1300 includes a cylindrical sleeve 1301, a hollow retaining shaft 1302 with a threaded distal end portion 1302a, a holding sleeve 1304 at a proximal end and a safety shield 1306 that is slidable along an outside of the holding sleeve 1304. The holding sleeve 1304 includes an anti-splay ring 1340 at its distal end to laterally retain the tissue retractors 200, 300 in an assembled configuration. The safety shield 1306 includes several spring arms 1306a that are selectively engageable with a first groove 1304a in an actuating position (FIG. 21B) and a second groove (not shown) in a safety position (FIG. 21A) on the external surface of the holding sleeve 1304. The holding sleeve 1304 also includes an actuating window 1304c that exposes an actuator 1302a on an external surface of the retaining shaft 1302.

In use, the safety shield 1306 is moved to an actuating position wherein the spring arms 1306a engage the first groove 1304a to secure the safety shield 1306 in the actuating position. The threaded end portion 1302a of the retaining shaft 1302 is engaged with the internal threaded portion 114 of the arms 110 by manipulating the actuator 1302a through the actuating window 1304c, which is exposed when the safety shield 1306 is in the actuating position. The tissue retractors 200, 300 are attached to the holder 1300 such that the proximal end portion 204 is positioned under the anti-splay ring 1340. The polyaxial screw 100 and the holder 1300 are guided to the surgical site through the generally conical incision CI by a K-wire (not shown). When a tip of the bone screw 104 contacts the vertebra V, the screwdriver 500 may be inserted down the hollow retaining shaft 1302 to drive the polyaxial screw 100 into the vertebra V. When the screwdriver 500 is driving the screw 104 into the vertebra V, the safety shield 306 is moved to the safety position covering the actuating window 1304c and the actuator 1302a to prevent a surgeon from moving the actuator 1302a and disengaging the retaining shaft 1302 from the polyaxial pedicle screw 100. The surgeon grasps the holder 1300 at the safety shield 1306 and the holding sleeve 1304 and drive the polyaxial screw 100 into the vertebra V. The safety shield 1306 is then moved from the safety position to the actuating position, where the spring arms 1306a engage the first groove 1304a to retain the safety shield 1306 in the safety position. The actuator 1302a is manipulated to rotate the retaining shaft 1302 and disengage the distal threads 1302a from the internal threaded portions 114 of the arms 110. The holder 1300 is removed from the generally conical incision CI leaving the polyaxial screw 100 and tissue retractors 200, 300 in the generally cylindrical incision CI.

Referring to FIGS. 6A, 6B, 12 and 22, the exemplary instrument set also includes a cap tray 1600 for storage and staging of the locking caps 700. The cap tray 1600 of the exemplary embodiment includes six cap stations 1602 that each receive an individual locking cap 700. The cap tray 1600 is not limited to the inclusion of six cap stations 1602 and may include nearly any number of cap stations 1602 that is desired by the use for storing a desired number of locking caps 700. Each of the cap stations 1602 includes a centrally located pedestal 1604 with an arcuate top surface that mates with the actuate surface 704a of the saddle portion 704, four alignment ribs 1606 and two button grooves 1608. The alignment ribs 1606 cooperate with the blocking tabs 408 and the arm 422 to align the arms 706, 708 of the saddle 704 generally perpendicular to the indicias 432 such that the saddle 704 is aligned to engage the rod R when the cap guide 400 is positioned in the partial pathway 206. The button groove 1608 receives the guide button 426 of the cap guide 400 to ensure alignment of the saddle 704 with the cap guide 400 for receipt of the rod R.

In use, the cap guide 400 or any other instrument of the exemplary instrument set, including the distractor 1000 or compressor 1101 that receive and retain the locking caps 700 therein, may stab and grab the locking caps 700 directly from the cap tray 1600. Specifically, the user grasp the cap guide 400 and stabs the locking cap 700 that is positioned in one of the cap stations 1602. The features at the distal end of the cap guide 400 cooperate with the features in the individual cap station 1602 to align and properly position the locking caps 700 at the distal end portion 402 of the cap guide 400. The cap tab 414 engages the threads 712 of the locking cap 700 to coaxially align the locking cap 700 with the hollow cavity 406. Therefore, when the cap guide 400 with a locking cap 700 secured in the distal end is introduced into the partial pathway 206 and the saddle 704 engages the rod R, the saddle 704 is pre-oriented to engage the rod R and the threads 712 are pre-oriented to engage the threaded portions 114 of the arms 110. Such a configuration may ease insertion of the locking cap 700 onto the body 102 and diminishes any possibility that the threads 712 of the locking cap 700 cross-thread with the threaded portions 114 of the arms 110, due to the pre-orientation of the locking cap 700 relative to the body 102.

Referring to FIGS. 1-22, in use, the polyaxial bone screw 100 is coupled to the tissue retractor 200 by sliding the distal end portion 202 of the tissue retractor 200 over the body 102 until the attachment tabs 212 mate with the corresponding recesses 116 of the body 102. Lower or distal surfaces of the attachment tabs 212 are tapered in a ramp-like configuration such that the top edge of the arms 110 urge the attachment tabs 212 from the relaxed position to the flexed position to allow the attachment tabs 212 to move over and past the locking edge 117 into the recesses 116. The polyaxial bone screw 100 is fixed to a vertebra V of a patient (FIG. 21), typically guided by the K-wire. The polyaxial pedicle screws 100 and the tissue retractors 200, 300 are inserted into the generally conical incision CI using the holder 1300, as was described above. Adjacent tissue retractors 200 move to the nested configuration (FIG. 10B) under the urging of the surgeon and the patient's soft tissue T. A portion of the rod R is inserted through the tissue retractor 200 until the rod R is seated in the rod receiving portion 112 of the polyaxial bone screw 100.

The locking cap 700 is positioned within one of the cap stations 1602 of the cap tray 1600 such that the saddle portion 704 is in an aligned configuration with respect to the tray 1600. The distal end portion 402 of the cap guide 400 is placed over the locking cap 700 in the tray 1600 to receive the locking cap 700. By virtue of the locking cap 700 having been previously aligned within the tray 1600, the saddle portion 704 of the locking cap 700 is aligned within the cap guide 400 when the cap guide 400 receives the locking cap 700 from the tray 800. That is, the arms 706, 708 of the locking cap 700 align with the slots 410 in the cap guide 400. The locking cap 700 is inserted through the tissue retractor 200 using the cap guide 400 until the cavity 710 in the saddle portion 704 of the locking cap 700 mates with the rod R and the threaded portion 702 thereof is received by the threaded portions 114 of the body 102 of the polyaxial bone screw 100.

As is described above, the locking cap 700 is aligned with and positioned for engagement within the partial pathway 206 of the tissue retractor 200 without ever coming into contact with the screwdriver 500. Although the screwdriver 500 generally includes a self-retaining feature when engaged to the locking cap 700, such a feature is typically less stable than the above-described engagement between the locking cap 700 and the cap guide 400. Specifically, when the cap guide 400 is moving downwardly through the partial pathway 206, the locking cap 700 is generally surrounded and protected from disengagement forces by the distal end portion 402 of the cap guide 400. Therefore, risk of the locking cap 700 disengaging from the cap guide 400 during insertion through the partial pathways 206 of the tissue retractors 200 in the assembled and implanted positions is less likely than situations where the locking cap 700 is self-retained by the screwdriver 500, inserted through the generally conical incision CI and into engagement with the body 102. Disengagement of the locking cap 700 from any instrument while in the conical incision CI is unfavorable as the locking cap 700 must be retrieved through the minimally invasive, generally conical incision CI. The engagement of the locking cap 700 with the distractor 1000, the compressor 1100, the threaded persuader 1500 or other similar instruments provides similar retaining protections to the locking cap 700.

Generally, concurrently with the locking cap 700 being received by the body 102, the cap guide 400 is coupled to the tissue retractor 200 to rotatably fix the tissue retractor 200 to the cap guide 400 by mating the blocking ribs 228 of the tissue retractor 200 with the corresponding blocking tabs 408 of the cap guide 400. The drive shaft 504 is then inserted into the hollow cavity 406 of the cap guide 400 to mate with the locking cap 700. The surgeon can now perform initial tightening of the locking cap 700 within the body 102 to at least provisionally secure the rod R to the polyaxial screw assembly 100.

Once the locking cap 700 is provisionally tightened, any manipulation of the position of the polyaxial bone screw 100 with respect to the rod R, such as compression or distraction with another polyaxial bone screw 100, can be performed without removing the drive shaft 504 from the hollow cavity 406 of the cap guide 400, assuming the locking cap 700 is inserted utilizing the distractor 1000 or compressor 1100, respectively. The counter-torque handle 600 is coupled to the cap guide 400 by inserting the drive shaft 504 into the open-ended slot 610 of the counter-torque handle 600 and inserting the instrument interface 606 into the hollow cavity 406 of the cap guide 400, typically by mating the splines 608*b* of the counter-torque handle 600 with the complementary splines 412 of the cap guide 400. In this configuration, the drive shaft 504 is rotatable within the counter-torque handle 600. Final tightening of the locking cap 700 is performed, such that the locking cap 700 bears against the rod R, by rotating the drive shaft 504. The rod R is thereafter fixed with respect to the polyaxial bone screw 100 and the torque input to the polyaxial pedicle screw assembly 100 by the screwdriver 500 is reacted through the body 102, the bulked-up portion 203 of the tissue retractor 200 between the blocking ribs 228 and the screw engagement ribs 214, the stiff and strong sleeve 401 of the cap guide 400 and the counter-torque handle 600. Accordingly, the relatively thin body 201 of the tissue retractor 200 and the arms 110 do not react significant portions of the final tightening forces and only react the forces over short distances adjacent the top end of the arms 110.

It will be appreciated by those skilled in the art that changes could be made to the exemplary embodiment described above without departing from the broad concept thereof. It is understood, therefore, that the described device and method are not limited to the particular embodiment disclosed, but it are intended to cover modifications within the spirit and scope of the exemplary embodiment as defined by the appended claims.

What is claimed:

1. A system for use in minimally invasive spine surgery, the system comprising:

a bone anchor having first and second arms that are spaced from one another along a first direction so as to define a rod-receiving channel between the first and second arms;

a first tissue retractor that is directly joined to the first arm and extends from the first arm but not the second arm along a second direction that is perpendicular to the first direction, the first tissue retractor defining a first concave inner surface that defines a first partial pathway, and the first tissue retractor extending along a first tissue retractor length along the second direction from the first arm to a free end of the first tissue retractor; and a second tissue retractor that is directly joined to the second arm and extends from the second arm but not the first arm along the second direction, the second tissue retractor defining a second concave inner surface that faces the first concave inner surface and defines a second partial pathway, and the second tissue retractor extending along a second tissue retractor length along the second direction from the second arm to a free end of the second tissue retractor, wherein in cross section perpendicular to the second direction, an entirety of the first tissue retractor is aligned with the first arm along the second direction along an entirety of a first major length that spans a majority of the first tissue retractor length along the second direction, and wherein in cross section perpendicular to the second direction, an entirety of the second tissue retractor is aligned with the second arm along the second direction along an entirety of a second major length that spans a majority of the second tissue retractor length along the second direction.

2. The system of claim 1, wherein the bone anchor defines a plane that extends between the first and second arms, and the tissue retractor is disposed entirely on one side of the plane.

3. The system of claim 1, wherein the tissue retractor includes a resiliently movable arm that is movable between an engaged position and a flexed position, and the resiliently movable arm extends from one of the first and second arms of the bone anchor.

4. The system of claim 1, further comprising a rod sized to be inserted between the first and second tissue retractors and into the rod-receiving channel of the bone anchor along the second direction, such that the rod is elongate along a third direction that is perpendicular to both the first and second directions.

5. The system of claim 1, further comprising:

an instrument configured to move at least one of the first bone anchor and a second bone anchor implanted in a second vertebra relative to one another, the instrument comprising:

a sleeve having a distal sleeve end configured to removeably couple to the first tissue retractor, and a proximal sleeve end spaced from the distal end, the sleeve defining a hollow cavity that extends between the proximal and distal ends of the sleeve, and the sleeve configured to be removably couplable to the first tissue retractor within the first partial pathway;

a pivoting arm that is pivotally mounted to the sleeve; and a ratchet mechanism configured to move the pivoting arm relative to the sleeve so as to cause at least one of the first and second bone anchors to move relative to the other of the first and second bone anchors.

6. The system of claim 5, wherein the first tissue retractor comprises at least one resiliently movable arm configured to engage the first bone anchor so as to couple the tissue retractor to the first bone anchor, and the sleeve defines at least one slot at the distal sleeve end portion, wherein each of the at least one slot is aligned with one of the at least one resiliently movable arms.

7. The system of claim 5, wherein the proximal sleeve end is configured to engage a counter-torque handle such that the sleeve and counter-torque handle are rotatably fixed relative to one another.

8. The system of claim 5, wherein the instrument is a distractor that is configured to move the pivoting arm relative to the sleeve so as to cause at least one of the first and second bone anchors to move away from the other of the at least one of the first and second bone anchors.

9. The system of claim 8, wherein a distal end of the pivoting arm includes a blunt end portion configured to engage the second bone anchor.

10. The system of claim 5, wherein the instrument is a compressor that is configured to move the pivoting arm relative to the sleeve so as to cause at least one of the first and second bone anchors to move towards the other of the at least one of the first and second bone anchors.

11. A method comprising:

driving a bone anchor into bone, the bone anchor having first and second arms that are spaced from one another along a first direction so as to define a rod-receiving channel between the first and second arms, wherein a first tissue retractor extends from the first arm but not the second arm, such that a first inner surface of the tissue retractor is concave so as to define a first partial pathway, wherein the first tissue retractor extends along a first tissue retractor length in a second direction away from the first arm to a free end of the first tissue retractor, the second direction being perpendicular to the first direction, wherein a second tissue retractor extends from the second arm but not the first arm, such that a second inner surface of the second tissue retractor that faces the first inner surface is concave so as to define a second partial pathway, wherein the second tissue retractor extends along a second tissue retractor length in the second direction away from the second arm to a free end of the second tissue retractor, wherein in cross section perpendicular to the second direction, an entirety of the first tissue retractor is aligned with the first arm along a first major length that spans a majority of the first tissue retractor length along the second direction, and wherein in cross section perpendicular to the second direction, an entirety of the second tissue retractor is aligned with the second arm along a second major length that spans a majority of the second tissue retractor length along the second direction.

12. The method of claim 11, comprising the step of inserting a rod between the first and second tissue retractors and into the rod-receiving channel of the bone anchor along a second direction, perpendicular to the first direction such that the rod is elongate along a third direction, perpendicular to both the first and second directions.

13. The method of claim 12, further comprising the step of attaching a locking cap to the first and second arms, thereby securing the rod in the rod-receiving channel.

* * * * *